United States Patent
Ohtake et al.

(10) Patent No.: US 8,158,652 B2
(45) Date of Patent: Apr. 17, 2012

(54) SUBSTITUTED PYRIDONE DERIVATIVE

(75) Inventors: Norikazu Ohtake, Tsukuba (JP); Takuya Suga, Tsukuba (JP); Shigeru Tokita, Tsukuba (JP)

(73) Assignee: MSD K.K., Chiyoda-Ku (JP)

( * ) Notice: Subject to any disclaimer, the term of this patent is extended or adjusted under 35 U.S.C. 154(b) by 1088 days.

(21) Appl. No.: 11/792,110

(22) PCT Filed: Nov. 30, 2005

(86) PCT No.: PCT/JP2005/022407
§ 371 (c)(1),
(2), (4) Date: Feb. 25, 2008

(87) PCT Pub. No.: WO2006/059778
PCT Pub. Date: Jun. 8, 2006

(65) Prior Publication Data
US 2008/0269287 A1    Oct. 30, 2008

(30) Foreign Application Priority Data
Dec. 1, 2004    (JP) .................. 2004-348159

(51) Int. Cl.
*A61K 31/4545* (2006.01)
*C07D 213/64* (2006.01)

(52) U.S. Cl. ......... 514/318; 514/326; 546/193; 546/208

(58) Field of Classification Search ............ 514/318, 514/326; 546/193, 208
See application file for complete search history.

(56) References Cited

U.S. PATENT DOCUMENTS

| | | |
|---|---|---|
| 6,620,839 B2 | 9/2003 | Bennani et al. |
| 7,875,633 B2 * | 1/2011 | Naya et al. .............. 514/332 |
| 7,928,230 B2 * | 4/2011 | Wacker et al. ............ 544/324 |
| 2003/0181420 A1 | 9/2003 | Bayne et al. |
| 2005/0080111 A1 | 4/2005 | Bayne et al. |
| 2006/0025404 A1 | 2/2006 | Ancliff et al. |
| 2006/0178375 A1 | 8/2006 | Ohtake et al. |

FOREIGN PATENT DOCUMENTS
WO    WO 02/06223    1/2002

OTHER PUBLICATIONS

Bayne et al. "Preparation of pyridones . . . " CA139:133472 (2003).*
Nagato et al. "preparation of 1,2 . . . " CA136:53682 (2001).*
Naya et al. "Preparation of phenylpyridone . . . " CA146:295777 (2007).*
Norman "New H1/H3 antagonists . . . " Exp. Opin. Ther. Pat. 21(3) 425-429 (2011).*
Smith "Preparation of 2-pyridone . . . " CA139:36439 (2003).*
Xiao et al. "Discovery of a series . . . " Bioorg. Med. Chem. Lett. 21, p. 861-864 (2011).*
Becknell et al. "Synthesis and eval . . . " Bioorg. Med. Chem. Lett. v. 21, p. 7076-7080 (2011).*
Berlin et al. "Recent advan . . . " Expert Opin. Ther. Patents v. 17(6) p. 675-687 (2007).*

* cited by examiner

*Primary Examiner* — Celia Chang
(74) *Attorney, Agent, or Firm* — J. Eric Thies; Gerard M. Devlin

(57) ABSTRACT

Compounds of a formula (I)

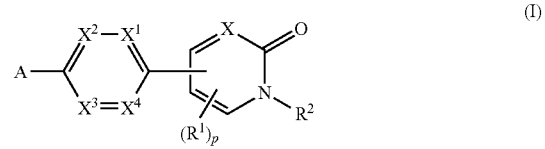

[wherein, A represents formula (III-1)

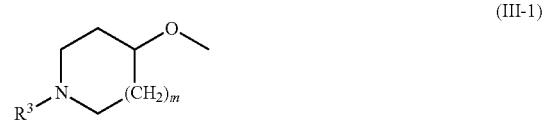

R3 is a hydrogen, lower alkyl et al; m is 0 or 1; R1 is a hydrogen atom, halogen atom et al, R2 is a hydrogen et al; p is 0 to 4; X is a carbon atom or nitrogen atom; and X1 to X4 is a lower alkyl et al], or pharmaceutical acceptable salts thereof. These have a potency antagonistic to binding to histamine H3 receptor, or have a potency inhibiting the constant activity of histamine H3 receptor, and are useful in the therapy of obesity, diabetes et al.

7 Claims, No Drawings

SUBSTITUTED PYRIDONE DERIVATIVE

CROSS REFERENCE TO RELATED APPLICATIONS

This application is a U.S. National Phase application under 35 U.S.C. §371 of PCT Application No. PCT/JP2005/022407, filed Nov. 30, 2005, which claims priority under 35 U.S.C. §119 from JP Application No. JP2004-348159, filed Dec. 12, 2004.

TECHNICAL FIELD

The present invention relates to substituted pyridone derivative useful in the field of medicines. The compounds act as a histamine-H3 receptor antagonistic substance or inverse-agonistic substance, and are useful as preventives or remedies for various circular system diseases, nervous system diseases, metabolic system diseases et al.

BACKGROUND ART

It has been known that, in organisms such as typically mammals, histamine that is a physiologically-active endogenous factor functions as a neurotransmitter and has extensive pharmacological activities (for example, see *Life Science*, Vol. 17, p. 503 (1975)).

Immunohistochemical studies have made it clear that a histamine-agonistic (producing) cell body exists in the nodal papillary nucleus in a posterior hypothalamic region and that histamine nerve fibers project in an extremely broad range in the brain, which supports various pharmacological effects of histamine (for example, see *Journal of Comprehensive Neurology*, Vol. 273, p. 283).

The existence of histamine-agonistic nerves in the nodal papillary nucleus in a posterior hypothalamic region suggests that histamine may have an important role in control of physiological functions relating to brain functions, especially to hypothalamic functions (sleep, vigilance rhythm, incretion, eating and drinking action, sexual action et al) (for example, see *Progress in Neurobiology*, Vol. 63, p. 637 (2001)).

The existence of the projection to the brain region that relates to vigilance sustenance, for example, to cerebral cortex, suggests the role in control of vigilance or vigilance-sleep cycle. The existence of the projection to many peripheral structures such as hippocampus and amygdaloid complex suggests the role in control of autonomic nerves, emotion, control of motivated action and learning/memory process.

When released from producing cells, histamine acts with a specific polymer that is referred to as a receptor on the surface of a cell membrane or inside a target cell, therefore exhibiting its pharmacological effects for control of various body functions. Heretofore, four types of histamine receptors have been found. In particular, the presence of a histamine receptor that participates in the central and peripheral nervous functions, a histamine-H3 receptor, has been shown by various pharmacological and physiological studies (for example, see *Trends in Pharmacological Science*, Vol. 8, p. 24 (1986)). Recently, human and rodent histamine-H3 receptor genes have been identified and their existence has been revealed (for example, see *Molecular Pharmacology*, Vol. 55, p. 1101 (1999)).

It is shown that a histamine-H3 receptor exists in the presynaptic membrane of central or peripheral neurocytes and functions as a self-receptor, therefore controlling the release of histamine and controlling even the release of other neurotransmitters. Specifically, it is reported that a histamine-H3 receptor agonist, or its antagonist or inverse-agonist controls the release of histamine, noradrenaline, serotonin, acetylcholine or dopamine from nerve terminal. For example, the release of these neurotransmitters is inhibited by an agonist such as (R)-(α)-methylhistamine, and is promoted by an antagonist or inverse-agonist such as thioperamide (for example, see *Trends in Pharmacological Science*, Vol. 19, p. 177 (1998)).

Recent studies have shown that a histamine-H3 receptor has extremely high homeostatic activities (activities observed in the absence of an endogenous agonistic factor, e.g., histamine) in the receptor-expressing cells/tissues or in a membrane fraction derived from the expressing cells/tissues and even in living bodies (for example, see *Nature*, Vol. 408, p. 860).

It is reported that these homeostatic activities are inhibited by an inverse-agonist. For example, thioperamide or syproxyfan inhibits the homeostatic self-receptor activity, and, as a result, promotes the release of neurotransmitters, for example, release and liberation of histamine from nerve terminal.

Regarding rats, a high-level selective inhibitor of histamine synthase (histidine decarboxylase) inhibits the vigilance of rats, and therefore it is shown that histamine participates in controlling motive vigilance. Regarding cats, administration of a histamine-H3 receptor agonist, (R)-(α)-methylhistamine to cats increases their deep slow-wave sleep (for example, see *Brain Research*, Vol. 523, p. 325 (1990)).

Contrary to this, a histamine-H3 receptor antagonist or inverse-agonist, thioperamide dose-dependently increases vigilance. In addition, thioperamide decreases slow-wave and REM sleep (see *Life Science*, Vol. 48, p. 2397 (1991)).

A histamine-H3 receptor antagonist or inverse-agonist, thioperamide or GT-2331 reduces emotional cataplexy and sleep of narcoleptic dogs (for example, see *Brain Research*, Vol. 793, p. 279 (1998)).

These informations suggest that the H3 receptor may participate in control of vigilance-sleep and in sleep disorder-associated diseases, further suggesting a possibility that a selective histamine-H3 agonist, antagonist or inverse-agonist may be useful for treatment of sleep disorders or various sleep disorder-associated diseases (for example, idiopathic hypersomnia, repetitive hypersomnia, true hypersomnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression, schizophrenia).

In animal experiments with rats, the administration of a histamine-H3 receptor antagonist or inverse-agonist, thioperamide or GT-2331 relieves the condition of learning disorder (LD) and attention deficit hyperactivity disorder (ADHD) (for example, see *Life Science*, Vol. 69, p. 469 (2001)). These informations suggest a possibility that the selective H3 agonist, antagonist or inverse-agonist may be useful for treatment and/or prevention of learning disorder or attention deficit hyperactivity disorder.

In animal experiments with rats, administration of histamine to their ventricle inhibits their eating action, therefore suggesting that histamine may participate in control of eating action (for example, see *Journal of Physiology and Pharmacology*, Vol. 49, p. 191 (1998)).

A histamine-H3 receptor antagonist or inverse-agonist, thioperamide dose-dependently inhibits eating action. In addition, thioperamide promotes intracerebral histamine release (for example, see *Behavioral Brain Research*, Vol. 104, p. 147 (1999)).

These informations suggest that a histamine H3 receptor may participate in eating action control, further suggesting that a histamine-H3 antagonist or inverse-agonist may be useful for prevention or remedy of metabolic system diseases such as eating disorder, obesity, diabetes, emaciation, hyperlipemia.

In animal experiments with rats, a histamine-H3 receptor agonist, (R)-(α)-methylhistamine dose-dependently lowers their basal diastolic pressure, and its action is antagonized by a histamine-H3 receptor antagonist or inverse-agonist, thioperamide (for example, see *European Journal of Pharmacology*, Vol. 234, p. 129, (1993)).

These informations suggest that a histamine-H3 receptor may participate in control of blood pressure, heart beat and cardiac output, further suggesting that a histamine-H3 receptor agonist, antagonist or inverse-agonist may be useful for prevention or remedy of circulatory system diseases such as hypertension and various cardiac disorders.

In animal experiments with rats, administration of a histamine-H3 receptor agonist, (R)-(α)-methylhistamine lowers their object cognitive and learning effects in the object cognition test and the passive turnout test with them. On the other hand, in a scopolamine-induced amnesia test, a histamine-H3 receptor antagonist or inverse-agonist, thioperamide dose-dependently relieves amnesia induced by the chemical (for example, see *Pharmacology, Biochemistry and Behavior*, Vol. 68, p. 735 (2001)).

These informations suggest a possibility that a histamine-H3 receptor antagonist or inverse-agonist may be useful for prevention or remedy of various diseases accompanied by memory/learning disorder, for example, Alzheimer's disease, Parkinson's disease or attention deficit/hyperactivity disorder.

In animal experiments with mice, a histamine-H3 receptor antagonist or inverse-agonist, thioperamide dose-dependently inhibits the spasm induced by electric shock or the epileptoid seizure induced by pentylene tetrazole (PTZ) (for example, see *European Journal of Pharmacology*, Vol. 234, p. 129 (1993), and *Pharmacology, Biochemistry and Behavior*, Vol. 68, p. 735 (2001)).

These informations suggest that a histamine-H3 receptor antagonist or inverse-agonist may be useful for prevention or remedy of epilepsy or central spasm.

As compounds structurally similar to those of formula (I) of the invention, for example, a compound of the following formula (A) is used as a production intermediate for β-carboline (see *Bioorganic & Medicinal Chemistry Letters*, Vol. 13, pp. 761-765, 2003):

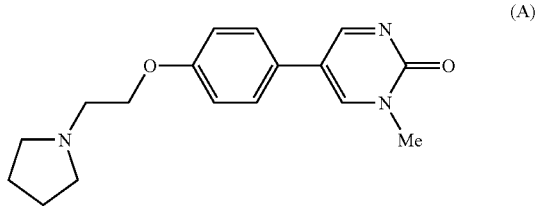

The reference describes only the usability of the compound of formula (A) as a production intermediate for β-carboline, but this has neither description nor suggestion indicating that the compound may have a histamine-H3 receptor antagonistic effect or inverse-agonistic effect.

The reference says that the use of the β-carboline compounds that are produced via the compound of formula (A) as their production intermediate is for a phosphodiesterase-5 (PDE5) inhibitor, and this has neither description nor suggestion indicating that the compounds may have a histamine-H3 receptor antagonistic effect or inverse-agonistic effect.

DISCLOSURE OF THE INVENTION

An object of the invention is to provide novel substituted pyridone derivatives having an effect of inhibiting histamine from binding to a histamine-H3 receptor or an activity of inhibiting the homeostatic activity that a histamine-H3 receptor has.

We, the present inventors have assiduously studied so as to develop compounds having an effect of inhibiting histamine from binding to a histamine-H3 receptor or an activity of inhibiting the homeostatic activity that a histamine-H3 receptor has, and have completed the present invention.

Specifically, the invention relates to the following:

(1) A compound represented by a formula (I) or pharmaceutically-acceptable salt thereof:

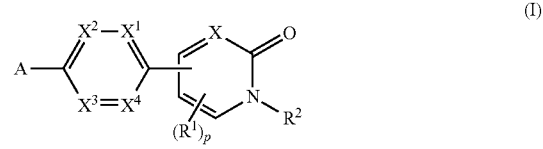

[wherein A represents a group of a formula (III-1):

or a formula (III-2):

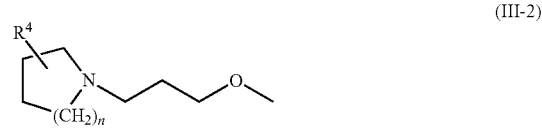

(wherein $R^3$ represents a hydrogen atom, or a cycloalkyl group optionally substituted with a lower alkyl group, a halo-lower alkyl group, a cycloalkyl group, a halogen atom or a hydroxyl group;

$R^4$ represents a hydrogen atom, a hydroxyl group, a halogen atom, a lower alkyl group, a halo-lower alkyl group, a lower alkoxy group, a halo-lower alkoxy group, a lower alkoxy-lower alkyl group, or a halo-lower alkoxy-lower alkyl group;

m indicates 0 or 1; n indicates 0, 1 or 2);

$R^1$ each independently represents a hydrogen atom, a hydroxyl group, a halogen atom, a lower alkyl group, a halo-lower alkyl group, a lower alkoxy group, a halo-lower alkoxy group, a lower alkoxy-lower alkyl group, or a halo-lower alkoxy-lower alkyl group;

$R^2$ represents a hydroxyl group, a halogen atom, a lower alkyl group, a halo-lower alkyl group, a lower alkoxy group, a halo-lower alkoxy group, a lower alkoxy-lower alkyl group, or a halo-lower alkoxy-lower alkyl group, or $R^2$ represents a group of the formula (II):

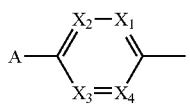
(II)

(wherein A has the same meaning as above) in the formula (I);
p indicates from 0 to 4;
X represents a carbon atom or a nitrogen atom;
$X^1$ to $X^4$ each independently represent a carbon atom optionally substituted with a lower alkyl group, a lower alkoxy group, a halo-lower alkoxy group or a halogen atom];

(2) The compound of above (1), which is represented by a formula (I-1) or pharmaceutically-acceptable salt thereof,

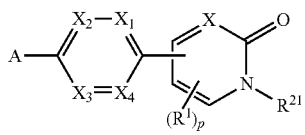
(I-1)

[wherein each symbols have the same meanings as above];

(3) The compound of above (1), which is represented by a formula (I-2) or pharmaceutically-acceptable salt thereof:

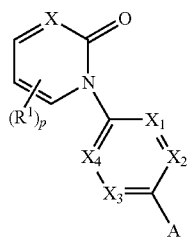
(I-2)

[wherein each symbols have the same meanings as above];

(4) The compound of above (1) or pharmaceutically-acceptable salt thereof, wherein X is a nitrogen atom;

(5) The compound of above (1) or pharmaceutically-acceptable salt thereof, wherein X is a carbon atom;

(6) The compound of above (2) or (3) or pharmaceutically-acceptable salt thereof, wherein A is represented by a formula (III-1):

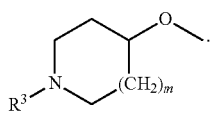
(III-1)

[wherein each symbols have the same meanings as above];

(7) The compound of above (2) or (3) or pharmaceutically-acceptable salt thereof, wherein A is represented by a formula (III-2):

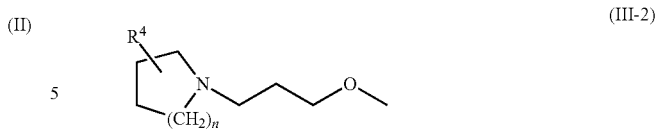
(III-2)

[wherein each symbols have the same meanings as above];

(8) The compound of above (1) or pharmaceutically-acceptable salt thereof, wherein the compound of formula (I) is the following:
1-methyl-5-{4-[3-(1-piperidinyl)propoxy]phenyl}-2(1H)-pyridone,
1-difluoromethyl-5-{4-[3-(1-piperidinyl)propoxy]phenyl}-2(1H)-pyridone,
1-difluoromethyl-4-{4-[3-(1-piperidinyl)propoxy]phenyl}-2(1H)-pyridone,
5-[4-(1-cyclopentylpiperidin-4-yloxy)phenyl]-1-methyl-2(1H)-pyridone,
5-[4-(1-cyclopentylpiperidin-4-yloxy)phenyl]-1-difluoromethyl-2(1H)-pyridone,
4-[4-(1-cyclopentylpiperidin-4-yloxy)phenyl]-1-difluoromethyl-2(1H)-pyridone,
4-[4-(1-cyclopentylpiperidin-4-yloxy)phenyl]-1-methyl-2(1H)-pyridone,
4-[4-(1-cyclopentylpiperidin-4-yloxy)phenyl]-1-ethyl-2(1H)-pyridone,
4-[4-(1-cyclopentylpiperidin-4-yloxy)phenyl]-1-(1-methylethyl)-2(1H)-pyridone,
4-[4-(1-cyclobutylpiperidin-4-yloxy)phenyl]-1-difluoromethyl-2(1H)-pyridone,
5-[4-(1-cyclopentylpiperidin-4-yloxy)phenyl]-1-methoxy-2(1H)-pyridone,
5-[4-(1-cyclopentylpiperidin-4-yloxy)phenyl]-1,3-dimethyl-2(1H)-pyridone,
4-[4-(1-cyclopentylpiperidin-4-yloxy)phenyl]-1-(2,2-difluoroethyl)-2(1H)-pyridone,
4-[4-(1-cyclopropylpiperidin-4-yloxy)phenyl]-1-difluoromethyl-2(1H)-pyridone,
6-[4-(1-cyclopentylpiperidin-4-yloxy)phenyl]-1-methyl-2(1H)-pyridone,
3-[4-(1-cyclopentylpiperidin-4-yloxy)phenyl]-1-methyl-2(1H)-pyridone,
1-[4-(1-cyclopentylpiperidin-4-yloxy)phenyl]-2(1H)-pyridone,
5-bromo-3-[4-(1-cyclopentylpiperidin-4-yloxy)phenyl]-1-methyl-2(1H)-pyridone,
1-[4-(1-cyclopentylpiperidin-4-yloxy)phenyl]-4-methyl-2(1H)-pyridone,
3-[4-(1-cyclopentylpiperidin-4-yloxy)phenyl]-1,6-dimethyl-2(1H)-pyridone,
5-[4-(1-cyclopentylpiperidin-4-yloxy)phenyl]-1,6-dimethyl-2(1H)-pyridone,
5-[4-(1-cyclopentylpiperidin-4-yloxy)phenyl]-1,4-dimethyl-2(1H)-pyridone,
5-chloro-3-[4-(1-cyclopentylpiperidin-4-yloxy)phenyl]-1-methyl-2(1H)-pyridone,
5-[4-(1-cyclopentylpiperidin-4-yloxy)phenyl]-1-methyl-2(1H)-pyrimidone,
5-[4-(1-cyclopentylpiperidin-4-yloxy)phenyl]-1-ethyl-2(1H)-pyridone,
5-[4-(1-cyclopentylpiperidin-4-yloxy)phenyl]-1-(1-methylethyl)-2(1H)-pyridone,
5-[4-(1-cyclopentylpiperidin-4-yloxy)phenyl]-1-ethyl-2(1H)-pyridone, 5-[4-(1-cyclopentylpiperidin-4-yloxy)phenyl]-1-(1-methylethyl)-2(1H)-pyrimidone,
5-[4-(1-cyclopentylpiperidin-4-yloxy)phenyl]-1-ethoxy-2(1H)-pyridone,
5-[4-(1-cyclobutylpiperidin-4-yloxy)phenyl]-1-methyl-2(1H)-pyridone,
3-chloro-4-[4-(1-cyclopentylpiperidin-4-yloxy)phenyl]-1 difluoromethyl-2(1H)-pyridone,
3-chloro-4-[4-(1-cyclobutylpiperidin-4-yloxy)phenyl]-1-difluoromethyl-2(1H)-pyridone,
5-[4-(1-cyclopentylpiperidin-4-yloxy)phenyl]-1-(2-fluoroethyl)-2(1H)-pyridone,
5-[4-(1-cyclobutylpiperidin-4-yloxy)phenyl]-1-(2-fluoroethyl)-2(1H)-pyridone,
5-[4-(1-cyclobutylpiperidin-4-yloxy)phenyl]-1-methoxy-2(1H)-pyridone,
5-[4-(1-(1-methylethyl)piperidin-4-yloxy)phenyl]-1-methoxy-2(1H)-pyridone,
4-[4-(1-cyclopentylpiperidin-4-yloxy)phenyl]-1-(2-hydroxyethyl)-2(1H)-pyridone,
5-[4-(1-cyclopentylpiperidin-4-yloxy)phenyl]-1-(1-methylethoxy)-2(1H)-pyridone,
5-[4-(1-(1-methylethyl)piperidin-4-yloxy)phenyl]-1-methyl-2(1H)-pyridone,
5-[4-(1-cyclopentylpiperidin-4-yloxy)phenyl]-1-(2-fluoroethoxy)-2(1H)-pyridone,
5-[4-(1-cyclobutylpiperidin-4-yloxy)phenyl]-1-(2-fluoroethoxy)-2(1H)-pyridone,
4-[4-(1-cyclopentylpiperidin-4-yloxy)phenyl]-1-(2-fluoroethyl)-2(1H)-pyridone,
4-[4-(1-cyclobutylpiperidin-4-yloxy)phenyl]-1-(2-fluoroethyl)-2(1H)-pyridone,
3-chloro-4-[4(1-cyclobutylpiperidin-4-yloxy)phenyl]-1-methyl-2(1H)-pyridone,
3-chloro-5-[4-(1-cyclobutylpiperidin-4-yloxy)phenyl]-1-methyl-2(1H)-pyridone,
1-methyl-4-{4-[3-(1-piperidinyl)propoxy]phenyl}-2(1H)-pyridone,
1-methyl-4-{4-[3-((2S)-2-methyl-1-pyrrolidinyl)propoxy]phenyl}-2(1H)-pyridone,
1-methyl-4-{4-[3-((2R)-2-methyl-1-pyrrolidinyl)propoxy]phenyl}-2(1H)-pyridone,
1-methyl-4-{4-[3-((3R)-3-methyl-1-piperidinyl)propoxy]phenyl}-2(1H)-pyridone,
1-ethyl-4-{4-[3-((3R)-3-methyl-1-piperidinyl)propoxy]phenyl}-2(1H)-pyridone,
1-methyl-5-{4-[3-((3R)-3-methyl-1-piperidinyl)propoxy]phenyl}-2(1H)-pyridone, or 1-ethyl-5-{4-[3-((3R)-3-methyl-1-piperidinyl)propoxy]phenyl}-2(1H)-pyridone;

(9) A histamine H3-receptor antagonist or inverse-agonist comprising a compound of any one of above (1) to (8) or pharmaceutically-acceptable salt thereof as the active ingredient.

(10) A histamine H3-receptor antagonist comprising a compound of any one of above (1) to (8) or pharmaceutically-acceptable salt thereof as the active ingredient.

(11) A histamine H3-receptor inverse-agonist comprising a compound of any one of above (1) to (8) or pharmaceutically-acceptable salt thereof as the active ingredient.

(12) A preventive and/or a remedy comprising a compound of any of above (1) to (8) or pharmaceutically-acceptable salt thereof as the active ingredient, which is for metabolic system diseases such as obesity, diabetes, hormone secretion disorder, hyperlipemia, gout and fatty liver; circulatory system diseases such as stenocardia, acute/congestive cardiac insufficiency, cardiac infarction, coronary arteriosclerosis, hypertension, nephropathy, sleep disorder, diseases accompanied by sleep disorder such as idiopathic hypersomnia, repetitive hypersomnia, true hypersomnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, electrolyte disorder; central or peripheral nervous system diseases such as bulimia, emotional disorder, depression, anxiety, epilepsy, delirium, dementia, schizophrenia, attention deficit/hyperactivity disorder, memory disorder, Alzheimer's disease, Parkinson's disease, sleep disorder, cognition disorder, motion disorder, paresthesia, dysosmia, epilepsy, morphine resistance, drug dependency, alcoholism; and tremor.

BEST MODE FOR CARRYING OUT THE INVENTION

The meanings of the terms used in this description are described, and the invention is described in more detail hereinunder.

"Lower alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group et al.

"Halogen atom" means, for example, a fluorine atom, a chlorine atom, a bromine atom or an iodine atom.

"Cycloalkyl group" is preferably a cycloalkyl group having from 3 to 9 carbon atoms, including, for example, a cyclopropyl group, a cyclobutyl group, a cyclopentyl group, a cyclohexyl group, a cycloheptyl group, a cyclooctyl group, a cyclononyl group.

"Lower alkoxy group" means a hydroxyl group of which the hydrogen atom is substituted with the above-mentioned lower alkyl group, including, for example, a methoxy group, an ethoxy group, a propoxy group et al.

"Halo-lower alkyl group" means the above-defined lower alkyl group substituted with from 1 to 3, the same or different, the above-defined halogen atoms, concretely including, for example, a 1-fluoroethyl group, a 2-fluoroethyl group, a 2-fluoro-1-methyl-ethyl group, a 3-fluoro-1-methyl-propyl group, a 2,2-difluoroethyl group, a 2,2,2-trifluoroethyl group, a 1-fluoromethyl-propyl group, a 3,3-difluoropropyl group, a 3,3,3-trifluoropropyl group, a 2-fluoro-1,1-dimethyl-ethyl group, a 1-chloroethyl group, a 2-chloroethyl group, a 2-chloro-1-methyl-ethyl group, a 3-chloro-1-methyl-propyl group, a 1-chloromethyl-propyl group, a 2-chloro-1,1-dimethyl-ethyl group et al.

"Halo-lower alkoxy group" means the above-defined lower alkoxy group substituted with from 1 to 3, the same or different, the above-defined halogen atoms, concretely including, for example, a 1-fluoroethoxy group, a 2-fluoroethoxy group, a 2-fluoro-1-methyl-ethoxy group, a 3-fluoro-1-methyl-propoxy group, a 2,2-difluoroethoxy group, a 2,2,2-trifluoroethoxy group, a 1-fluoromethyl-propoxy group, a 3,3-difluoropropoxy group, a 3,3,3-trifluoropropoxy group, a 2-fluoro-1,1-dimethyl-ethoxy group, 1-chloroethoxy group, a 2-chloroethoxy group, a 2-chloro-1-methyl-ethoxy group, a 3-chloro-1-methyl-propoxy group, a 1-chloromethyl-propoxy group, a 2-chloro-1,1-dimethyl-ethoxy group et al.

"Lower alkoxy-lower alkyl group" means the above-defined lower alkyl group substituted with the above-defined lower alkoxy group, concretely including, for example, a 1-methoxy-ethyl group, a 2-ethoxyethyl group, a 2-methoxy-1-methyl-ethyl group, a 3-methoxy-1-methyl-propyl group, a 1-methoxymethyl-propyl group, a 1,1-dimethyl-2-methoxy-ethyl group, a 4-methoxy-pentyl group, a 3-methoxy-pentyl group, a 2-methoxy-pentyl group, a 1-methoxy-pentyl group et al.

"Halo-lower alkoxy-lower alkyl group" means the above-defined lower alkoxy-lower alkyl group in which the lower alkoxy group is substituted with from 1 to 3, the same or different halogen atoms, and this includes, for example, a 2-(2-chloroethoxy)-ethyl group, a 2-chloro-methoxyethyl group, a 2-chloromethoxy-1-methyl-ethyl group, a 3-chloro-methoxy-1-methyl-propyl group, a 1-chloromethoxymethyl-propyl group, a 2-chloro-methoxy-1,1-dimethyl-ethyl group et al.

For more concretely disclosing the compounds of the above-mentioned formula (I) of the invention, the compounds of formula (I):

$$A-\underset{X^3=X^4}{\overset{X^2-X^1}{\diagup}}\diagdown\underset{(R^1)_p}{\overset{X}{\diagup}}\diagdown\underset{R^2}{N}\diagdown O \qquad (I)$$

[wherein each symbols have the same meanings as above] are described in more detail.

A represents a group of formula (III-1):

$$R^3-N\diagdown(CH_2)_m\diagdown O\diagdown \qquad (III-1)$$

or formula (III-2):

$$\underset{(CH_2)_n}{\overset{R^4}{\diagup}}N\diagdown\diagdown O\diagdown \qquad (III-2)$$

(wherein each symbols have the same meanings as above).

The group of formula (III-1) is described below.

m indicates 0 or 1, and of those, m is preferably 1.

$R^3$ represents a hydrogen atom, or a cycloalkyl group optionally substituted with a lower alkyl group, a halo-lower alkyl group, a cycloalkyl group, a halogen atom or a hydroxyl group.

The cycloalkyl group for $R^3$ includes those of the above-defined cycloalkyl group; of those, preferred are a cyclopropyl group, a cyclobutyl group, a cyclopentyl group or a cyclohexyl group; and more preferred are a cyclopropyl group, a cyclobutyl group and a cyclopentyl group.

The cycloalkyl group may have from 1 to 3 substituents of a lower alkyl group, a halo-lower alkyl group, a cycloalkyl group, a halogen atom or a hydroxyl group. When this has 2 or 3 substituents, the substituents may be the same or different.

The lower alkyl group for the substituent includes those of the above-defined alkyl group.

The halo-lower alkyl group for the substituent includes those of the above-defined halo-lower alkyl group.

The cycloalkyl group for the substituent includes those of the above-defined cycloalkyl group.

The halogen atom for the substituent includes those of the above-defined halogen atom.

The group of formula (III-1) concretely includes, for example, a 1-(1-methylcyclopropyl)piperidin-4-yloxy group, a 1-(1-ethylcyclopropyl)piperidin-4-yloxy group, a 1-(1-methylcyclobutyl)piperidin-4-yloxy group, a 1-(2-methylcyclopentyl)piperidin-4-yloxy group, a 1-(3-methylcyclopentyl)piperidin-4-yloxy group, a 1-(1-ethylcyclobutyl)piperidin-4-yloxy group, a (1-1-methylcyclopentyl)piperidin-4-yloxy group, a 1-(2-methylcyclopentyl)piperidin-4-yloxy group, a 1-(3-methylcyclopentyl)piperidin-4-yloxy group, a 1-(1-ethylcyclopentyl)piperidin-4-yloxy group, a 1-(1-methylcyclohexyl)piperidin-4-yloxy group, a 1-(2-methylcyclohexyl)piperidin-4-yloxy group, a 1-(3-methylcyclohexyl)piperidin-4-yloxy group, a (1-4-methylcyclohexyl)piperidin-4-yloxy group, a (1-(1-ethylcyclohexyl)piperidin-4-yloxy group, a 1-(1-methylcycloheptyl)piperidin-4-yloxy group, a 1-(1-ethylcycloheptyl)piperidin-4-yloxy group, a 1-(1-methylcyclooctyl)piperidin-4-yloxy group, a 1-(1-ethylcyclooctyl)piperidin-4-yloxy group, a 1-(2-fluorocyclopropyl)piperidin-4-yloxy group, a 1-(2-fluorocyclobutyl)piperidin-4-yloxy group, a 1-(3-fluorocyclobutyl)piperidin-4-yloxy group, a 1-(2-fluorocyclopentyl)piperidin-4-yloxy group, a 1-(3-fluorocyclopentyl)piperidin-4-yloxy group, a 1-(2-fluorocyclohexyl)piperidin-4-yloxy group, a 1-(3-fluorocyclohexyl)piperidin-4-yloxy group, a 1-(4-fluorocyclohexyl)piperidin-4-yloxy group, a 1-(2-fluorocycloheptyl)piperidin-4-yloxy group, a 1-(3-fluorocycloheptyl)piperidin-4-yloxy group, a 1-4-fluorocycloheptyl)piperidin-4-yloxy group, a 1-(2-fluorocyclooctyl)piperidin-4-yloxy group, a 1-(3-fluorocyclooctyl)piperidin-4-yloxy group, a 1-(4-fluorocyclooctyl)piperidin-4-yloxy group, a 1-(5-fluorocyclooctyl)piperidin-4-yloxy group, a 1-2-chlorocyclopropyl)piperidin-4-yloxy group, a 1-(3-chlorocyclobutyl)piperidin-4-yloxy group, a 1-(2-chlorocyclobutyl)piperidin-4-yloxy group, a 1-(2-chlorocyclopentyl)piperidin-4-yloxy group, a 1-(3-chlorocyclopentyl)piperidin-4-yloxy group, a 1-(2-chlorocyclohexyl)piperidin-4-yloxy group, a 1-(3-chlorocyclohexyl)piperidin-4-yloxy group, a 1-(4-chlorocyclohexyl)piperidin-4-yloxy group, a 1-(2-chlorocycloheptyl)piperidin-4-yloxy group, a 1-(3-chlorocycloheptyl)piperidin-4-yloxy group, a 1-(4-chlorocycloheptyl)piperidin-4-yloxy group, a 1-(2-chlorocyclooctyl)piperidin-4-yloxy group, a 1-(3-chlorocyclooctyl)piperidin-4-yloxy group, a 1-(4-chlorocyclooctyl)piperidin-4-yloxy group, a 1(5-chlorocyclooctyl)piperidin-4-yloxy group, a 1-(2-hydroxycyclopropyl)piperidin-4-yloxy group, a 1-(3-hydroxycyclobutyl)piperidin-4-yloxy group, a 1-(2-hydroxycyclobutyl)piperidin-4-yloxy group, a 142-hydroxycyclopentyl)piperidin-4-yloxy group, a 1-(3-hydroxycyclopentyl)piperidin-4-yloxy group, a 1-(2-hydroxycyclohexyl)piperidin-4-yloxy group, a 1-(3-hydroxycyclohexyl)piperidin-4-yloxy group, a 1-4-hydroxycyclohexyl)piperidin-4-yloxy group, a 1-(2-hydroxycycloheptyl)piperidin-4-yloxy group, a 1-(3-hydroxycycloheptyl)piperidin-4-yloxy group, a 1-(4-hydroxycycloheptyl)piperidin-4-yloxy group, a 1-(2-hydroxycyclooctyl)piperidin-4-yloxy group, a 1-(3-hydroxycyclooctyl)

piperidin-4-yloxy group, a 1-(4-hydroxycyclooctyl)piperidin-4-yloxy group, a 1-(5-hydroxycyclooctyl)piperidin-4-yloxy group, a 1-2-cyclopropylcyclopropyl)piperidin-4-yloxy group, a 1-(2-cyclobutylcyclopropyl)piperidin-4-yloxy group, a 1-(2-cyclopentylcyclopropyl)piperidin-4-yloxy group, a 1-(2-cyclopropylcyclobutyl)piperidin-4-yloxy group, a 1-(3-cyclopropylcyclobutyl)piperidin-4-yloxy group, a 1-(2-cyclopropylcyclopentyl)piperidin-4-yloxy group, a 1-(3-cyclopropylcyclopentyl)piperidin-4-yloxy group, a 1-(2-cyclopropylcyclopropyl)piperidin-4-yloxy group, a 1-(2-cyclobutylcyclopropyl)piperidin-4-yloxy group, a 1-(2-cyclopentylcyclopropyl)piperidin-4-yloxy group, a 1-(2-cyclobutylcyclobutyl)piperidin-4-yloxy group, a 1-(3-cyclobutylcyclobutyl)piperidin-4-yloxy group, a 1-(2-cyclobutylcyclopentyl)piperidin-4-yloxy group, a 1-(3-cyclobutylcyclopentyl)piperidin-4-yloxy group et al. Of those, preferred are a 1-(1-methylcyclopropyl)piperidin-4-yloxy group, a 1-(1-methylcyclobutyl)piperidin-4-yloxy group, a 1-(3-methylcyclobutyl)piperidin-4-yloxy group, a 1-(1-methylcyclopentyl)piperidin-4-yloxy group, a 1-(2-methylcyclopentyl)piperidin-4-yloxy group a 1-(3-methylcyclopentyl)piperidin-4-yloxy group, a 1-(2-fluorocyclopropyl)piperidin-4-yloxy group, a 1-(3-fluorocyclobutyl)piperidin-4-yloxy group, a 1-(3-fluorocyclopentyl)piperidin-4-yloxy group, a 1-(4-fluorocyclohexyl)piperidin-4-yloxy group, a 1-(3-hydroxycyclobutyl)piperidin-4-yloxy group, a 1-(2-hydroxycyclopentyl)piperidin-4-yloxy group, a 1-(3-hydroxycyclopentyl)piperidin-4-yloxy group, a 1-(3-hydroxycyclohexyl)piperidin-4-yloxy group, a 1-(4-hydroxycyclohexyl)piperidin-4-yloxy group.

The group of formula (III-2) is described below.

n indicates 0, 1 or 2; and of those, n is preferably 1 or 2.

$R^4$ represents a hydrogen atom, a hydroxyl group, a halogen atom, a lower alkyl group, a halo-lower alkyl group, a lower alkoxy group, a halo-lower alkoxy group, a lower alkoxy-lower alkyl group, or a halo-lower alkoxy-lower alkyl group.

The halogen atom for $R^4$ includes those of the above-defined halogen atom.

The lower alkyl group for $R^4$ includes those of the above-defined lower alkyl group.

The halo-lower alkyl group for $R^4$ includes those of the above-defined halo-lower alkyl group.

The lower alkoxy group for $R^4$ includes those of the above-defined lower alkoxy group.

The halo-lower alkoxy group for $R^4$ includes those of the above-defined halo-lower alkoxy group.

The lower alkoxy-lower alkyl group for $R^4$ includes those of the above-defined lower alkoxy-lower alkyl group.

The halo-lower alkoxy-lower alkyl group for $R^4$ includes those of the above-defined halo-lower alkoxy-lower alkyl group.

The group of formula (III-2) concretely includes, for example, a 3-(pyrrolidin-1-yl)propoxy group, a 3-(3-hydroxypiperidin-1-yl)-propoxy group, a 3-(3-chloropyrrolidin-1-yl)propoxy group, a 3-(3-fluoropyrrolidin-1-yl)propoxy group, a 3-(3-bromopyrrolidin-1-yl)propoxy group, a 3-(2-methylpyrrolidin-1-yl)propoxy group, a 3-(3-methylpyrrolidin-1-yl)propoxy group, a 3-(2-ethylpyrrolidin-1-yl)propoxy group, a 3-(3-ethylpyrrolidin-1-yl)propoxy group, a 3-(2-isopropylpyrrolidin-1-yl)propoxy group, a 3-(3-isopropylpyrrolidin-1-yl)propoxy group, a 3-(2-fluoromethyl)pyrrolidin-1-yl)propoxy group, a 3-(3-fluoroethyl)pyrrolidin-1-yl)propoxy group, a 3-(2-(1-fluoroethyl)pyrrolidin-1-yl)propoxy group, a 3-(3-(1-fluoroethyl)pyrrolidin-1-yl)propoxy group, a 3-(2-(2-fluoroethyl)pyrrolidin-1-yl)propoxy group, a 3-(3-(2-fluoroethyl)pyrrolidin-1-yl)propoxy group, a 3-(3-methoxypyrrolidin-1-yl)propoxy group, a 3-(3-ethoxypyrrolidin-1-yl)propoxy group, a 3-(3-2-fluoroethoxy)pyrrolidin-1-yl)propoxy group, a 3-(2-(1-methoxyethyl)pyrrolidin-1-yl)propoxy group, a 3-(3-(1-methoxyethyl)pyrrolidin-1-yl)propoxy group, a 3-(2-(2-methoxyethyl)pyrrolidin-1-yl)propoxy group, a 3-(3-(2-methoxyethyl)pyrrolidin-1-yl)propoxy group, a 3-(2-(2-(2-chloroethoxy)ethyl)pyrrolidin-1-yl)propoxy group, a 3-(3-2-(2-chloroethoxy)-ethyl)pyrrolidin-1-yl)propoxy group, a 3-(piperidin-1-yl)propoxy group, a 3-(3-hydroxypiperidin-1-yl)propoxy group, a 3-(4-hydroxypiperidin-1-yl)propoxy group, a 3-(3-chloropiperidin-1-yl)propoxy group, a 3-(4-hydroxypiperidin-1-yl)propoxy group, a 3-(4-fluoropiperidin-1-yl)propoxy group, a 3-(3-hydroxypiperidin-1-yl)propoxy group, a 3-(4-hydroxypiperidin-1-yl)propoxy group, a 3-(3-bromopiperidin-1-yl)propoxy group, a 3-(4-bromopiperidin-1-yl)propoxy group, a 3-(2-methylpiperidin-1-yl)propoxy group, a 3-(3-methylpiperidin-1-yl)propoxy group, a 3-(4-methylpiperidin-1-yl)propoxy group, a 3-(2-ethylpiperidin-1-yl)propoxy group, a 3-(4-ethylpiperidin-1-yl)propoxy group, a 3-(2-isopropylpiperidin-1-yl)propoxy group, a 3-(3-isopropylpiperidin-1-yl)propoxy group, a 3-(4-isopropylpiperidin-1-yl)propoxy group, a 3-(2-(fluoromethyl)piperidin-1-yl)propoxy group, 3-(3-fluoromethyl)piperidin-1-yl)propoxy group, a 3-(4-(fluoromethyl)piperidin-1-yl)propoxy group, a 3-(2-(1-fluoroethyl)piperidin-1-yl)propoxy group, a 3-(3-(1-fluoroethyl)piperidin-1-yl)propoxy group, a 3-(4-(1-fluoroethyl)piperidin-1-yl)propoxy group, a 3-(2-(2-fluoroethyl)piperidin-1-yl)propoxy group, a 3-(3-(2-fluoroethyl)piperidin-1-yl)propoxy group, a 3-(4-(2-fluoroethyl)piperidin-1-yl)propoxy group, a 3-(3-methoxypiperidin-1-yl)propoxy group, a 3-(4-methoxypiperidin-1-yl)propoxy group, a 3-(3-ethoxypiperidin-1-yl)propoxy group, a 3-(4-ethoxypiperidin-1-yl)propoxy group, a 3-(3-(1-fluoroethoxy)piperidin-1-yl)propoxy group, a 3-(4-(1-fluoroethoxy)piperidin-1-yl)propoxy group, a 3-(3-(2-fluoroethoxy)piperidin-1-yl)propoxy group, a 3-(4-(2-fluoroethoxy)piperidin-1-yl)propoxy group, a 3-(3-(difluoromethoxy)piperidin-1-yl)propoxy group, a 3-(4-(difluoromethoxy)piperidin-1-yl)propoxy group, a 3-(3-(2-fluoro-1-methylethoxy)piperidin-1-yl)propoxy group, a 3-(4-(2-fluoro-1-methyl-ethoxy)piperidin-1-yl)propoxy group, a 3-(2-(1-methoxyethyl)piperidin-1-yl)propoxy group, a 3-(3-(1-methoxyethyl)piperidin-1-yl)propoxy group, a 3-(4-(1-methoxyethyl)piperidin-1-yl)propoxy group, a 3-(2-(2-methoxyethyl)piperidin-1-yl)propoxy group, a 3-(3-(2-methoxyethyl)piperidin-1-yl)propoxy group, a 3-(4-(2-methoxyethyl)piperidin-1-yl)propoxy group, a 3-(2-(2-(2-chloroethoxy)-ethyl)piperidin-1-yl)propoxy group, a 3-(3-(2-(2-chloroethoxy)-ethyl)piperidin-1-yl)propoxy group, a 3-(4-(2-(2-chloroethoxy)ethyl)piperidin-1-yl)propoxy group et al.

$X^1$ to $X^4$ each independently represent a carbon atom optionally substituted with a lower alkyl group, a lower alkoxy group, a halo-lower alkoxy group or a halogen atom.

The lower alkyl group for the substituent includes those of the above-defined lower alkyl group.

The lower alkoxy group for the substituent includes those of the above-defined lower alkoxy group.

The halo-lower alkoxy group for the substituent includes those of the above-defined halo-lower alkoxy group.

The halogen atom for the substituent includes those of the above-defined halogen atom.

Preferably, $X^1$ to $X^4$ are unsubstituted carbon atoms.

$R^1$ represents a hydrogen atom, a hydroxyl group, a halogen atom, a lower alkyl group, a halo-lower alkyl group, a lower alkoxy group, a halo-lower alkoxy group, a lower alkoxy-lower alkyl group, or a halo-lower alkoxy-lower alkyl group.

The halogen atom for $R^1$ includes those of the above-defined halogen atom.

The lower alkyl group for $R^1$ includes those of the above-defined lower alkyl group.

The halo-lower alkyl group for $R^1$ includes those of the above-defined halo-lower alkyl group.

The lower alkoxy group for $R^1$ includes those of the above-defined lower alkoxy group.

The halo-lower alkoxy group for $R^1$ includes those of the above-defined halo-lower alkoxy group.

The lower alkoxy-lower alkyl group for $R^1$ includes those of the above-defined lower alkoxy-lower alkyl group.

The halo-lower alkoxy-lower alkyl group for $R^1$ includes those of the above-defined halo-lower alkoxy-lower alkyl group.

$R^2$ represents a hydroxyl group, a halogen atom, a lower alkyl group, a halo-lower alkyl group, a lower alkoxy group, a halo-lower alkoxy group, a lower alkoxy-lower alkyl group, or a halo-lower alkoxy-lower alkyl group, or $R^2$ represents a group of formula (II) in the formula (I):

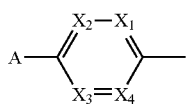
(II)

(wherein A has the same meaning as above).

The halogen atom for $R^2$ includes those of the above-defined halogen atom.

The lower alkyl group for $R^2$ includes those of the above-defined lower alkyl group.

The halo-lower alkyl group for $R^2$ includes those of the above-defined halo-lower alkyl group.

The lower alkoxy-lower alkyl group for $R^2$ includes those of the above-defined lower alkoxy-lower alkyl group.

The halo-lower alkoxy-lower alkyl group for $R^2$ includes those of the above-defined halo-lower alkoxy-lower alkyl group.

The case where $R^2$ is a group of formula (II) in formula (I) means that the compounds of formula (I) are compounds represented by a formula (I-2):

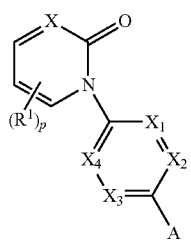
(I-2)

[wherein each symbols have the same meanings as above].

$R^2$ is preferably a haloalkyl group, a lower alkyl group, a lower alkoxy group or a lower alkoxy-lower alkyl group, or the group of formula (II).

X represents a carbon atom or a nitrogen atom.

p indicates from 0 to 4.

The formula (I) includes compounds of formula (I-1):

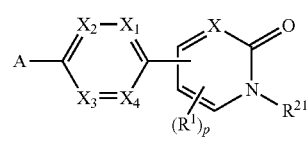
(I-1)

[wherein each symbols have the same meanings as above], or compounds of formula (I-2):

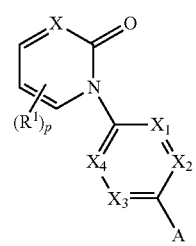
(I-2)

[wherein each symbols have the same meanings as above].

Another embodiment of the invention is a compound of formula (I) wherein X is a nitrogen atom, or X is a carbon atom.

Another embodiment of the invention is a compound of formula (I-1) or (I-2) wherein A is a group of a formula (III-1):

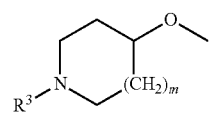
(III-1)

[wherein each symbols have the same meanings as above], or a group of a formula (III-2):

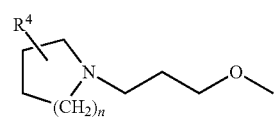
(III-2)

[wherein each symbols have the same meanings as above].

The compounds of the formula (I), (I-1) or (I-2) of the invention concretely include, for example, the following:
1-methyl-5-{4-[3-(1-piperidinyl)propoxy]phenyl}-2(1H)-pyridone,
1-difluoromethyl-5-{4-[3-(1-piperidinyl)propoxy]phenyl}-2(1H)-pyridone,
1-difluoromethyl-4-{4-[3-(1-piperidinyl)propoxy]phenyl}-2(1H)-pyridone,
5-[4-(1-cyclopentylpiperidin-4-yloxy)phenyl]-1-methyl-2(1H)-pyridone,
5-[4-(1-cyclopentylpiperidin-4-yloxy)phenyl]-1-difluoromethyl-2(1H)-pyridone,
4-[4-(1-cyclopentylpiperidin-4-yloxy)phenyl]-1-difluoromethyl-2(1H)-pyridone,
4-[4-(1-cyclopentylpiperidin-4-yloxy)phenyl]-1-methyl-2(1H)-pyridone, 4-[4-(1-cyclopentylpiperidin-4-yloxy)phenyl]-1-ethyl-2 (1H)-pyridone,
4-[4-(1-cyclopentylpiperidin-4-yloxy)phenyl]-1-(1-methylethyl)-2(1H)-pyridone,
4-[4-(1-cyclobutylpiperidin-4-yloxy)phenyl]-1-difluoromethyl-2(1H)-pyridone,
5-[4-(1-cyclopentylpiperidin-4-yloxy)phenyl]-1-methoxy-2 (1H)-pyridone,
5-[4-(1-cyclopentylpiperidin-4-yloxy)phenyl]-1,3-dimethyl-2(1H)-pyridone,
4-[4-(1-cyclopentylpiperidin-4-yloxy)phenyl]-1-(2,2-difluoroethyl)-2(1H)-pyridone,
4-[4-(1-cyclopropylpiperidin-4-yloxy)phenyl]-1-difluoromethyl-2(1H)-pyridone,
6-[4-(1-cyclopentylpiperidin-4-yloxy)phenyl]-1-methyl-2 (1H)-pyridone,
3-[4-(1-cyclopentylpiperidin-4-yloxy)phenyl]-1-methyl-2 (1H)-pyridone,
1-[4-(1-cyclopentylpiperidin-4-yloxy)phenyl]-2(1H)-pyridone,
5-bromo-3-[4-(1-cyclopentylpiperidin-4-yloxy)phenyl]-1-methyl-2(1H)-pyridone,
1-[4-(1-cyclopentylpiperidin-4-yloxy)phenyl]-4-methyl-2 (1H)-pyridone,
3-[4-(1-cyclopentylpiperidin-4-yloxy)phenyl]-1,6-dimethyl-2(1H)-pyridone,
5-[4-(1-cyclopentylpiperidin-4-yloxy)phenyl]-1,6-dimethyl-2(1H)-pyridone,
5-[4-(1-cyclopentylpiperidin-4-yloxy)phenyl]-1,4-dimethyl-2(1H)-pyridone,
5-chloro-3-[4-(1-cyclopentylpiperidin-4-yloxy)phenyl]-1-methyl-2(1H)-pyridone,
5-[4-(1-cyclopentylpiperidin-4-yloxy)phenyl]-1-methyl-2 (1H)-pyrimidone,
5-[4-(1-cyclopentylpiperidin-4-yloxy)phenyl]-1-ethyl-2 (1H)-pyridone,
5-[4-(1-cyclopentylpiperidin-4-yloxy)phenyl]-1-(1-methylethyl)-2(1H)-pyridone,
5-[4-(1-cyclopentylpiperidin-4-yloxy)phenyl]-1-ethyl-2 (1H)-pyrimidone,
5-[4-(1-cyclopentylpiperidin-4-yloxy)phenyl]-1-(1-methylethyl)-2(1H)-pyrimidone,
5-[4-(1-cyclopentylpiperidin-4-yloxy)phenyl]-1-ethoxy-2 (1H)-pyridone,
5-[4-(1-cyclobutylpiperidin-4-yloxy)phenyl]-1-methyl-2 (1H)-pyridone,
3-chloro-4-[4-(1-cyclopentylpiperidin-4-yloxy)phenyl]-1-difluoromethyl-2(1H)-pyridone,
3-chloro-4-[4-(1-cyclobutylpiperidin-4-yloxy)phenyl]-1-difluoromethyl-2(1H)-pyridone,
5-[4-(1-cyclopentylpiperidin-4-yloxy)phenyl]-1-(2-fluoroethyl)-2(1H)-pyridone,
5-[4-(1-cyclobutylpiperidin-4-yloxy)phenyl]-1-(2-fluoroethyl)-2(1H)-pyridone,
5-[4-(1-cyclobutylpiperidin-4-yloxy)phenyl]-1-methoxy-2 (1H)-pyridone,
5-[4-(1-(1-methylethyl)piperidin-4-yloxy)phenyl]-1-methoxy-2(1H)-pyridone,
4-[4-(1-cyclopentylpiperidin-4-yloxy)phenyl]-1-(2-hydroxyethyl)-2(1H)-pyridone,
5-[4-(1-cyclopentylpiperidin-4-yloxy)phenyl]-(1-methylethoxy)-2(1H)-pyridone,
5-[4-(1-(1-methylethyl)piperidin-4-yloxy)phenyl]-1-methyl-2(1H)-pyridone,
5-[4-(1-cyclopentylpiperidin-4-yloxy)phenyl]-1-(2-fluoroethoxy)-2(1H)-pyridone,
5-[4-(1-cyclobutylpiperidin-4-yloxy)phenyl]-1-(2-fluoroethoxy)-2(1H)-pyridone,
4-[4-(1-cyclopentylpiperidin-4-yloxy)phenyl]-1-(2-fluoroethyl)-2(1H)-pyridone,
4-[4-(1-cyclobutylpiperidin-4-yloxy)phenyl]-1-(2-fluoroethyl)-2(1H)-pyridone,
3-chloro-4-[4-(1-cyclobutylpiperidin-4-yloxy)phenyl]-1-methyl-2(1H)-pyridone,
3-chloro-5-[4-(1-cyclobutylpiperidin-4-yloxy)phenyl]-1-methyl-2(1H)-pyridone,
1-methyl-4-{4-[3-(1-piperidinyl)propoxy]phenyl}-2(1H)-pyridone,
1-methyl-4-{4-[3-((2S)-2-methyl-1-pyrrolidinyl)propoxy]phenyl}-2(1H)-pyridone,
1-methyl-4-{4-[3-((2R)-2-methyl-1-pyrrolidinyl)propoxy]phenyl}-2(1H)-pyridone,
1-methyl-4-{4-[3-((3R)-3-methyl-1-piperidinyl)propoxy]phenyl}-2(1H)-pyridone,
1-ethyl-4-{4-[3-((3R)-3-methyl-1-piperidinyl)propoxy]phenyl}-2(1H)-pyridone,
1-methyl-5-{4-[3-((3R)-3-methyl-1-piperidinyl)propoxy]phenyl}-2(1H)-pyridone,   1-ethyl-5-{4-[3-((3R)-3-methyl-1-piperidinyl)propoxy]phenyl}-2(1H)-pyridone, and their pharmaceutically-acceptable salts.

The compounds and pharmaceutically-acceptable salts thereof of the invention have an effect as a histamine-H3 acceptor antagonist or inverse-agonist.

"Histamine-H3 receptor inverse-agonist" as referred to herein means a receptor-binding substrate that has an effect completely or partially opposite to the effect of a histamine-H3 receptor antagonist, and is a ligand capable of inhibiting the homeostatic activity of a histamine-H3 receptor.

Methods for producing the compounds of the invention are described below.

The compounds (1) of the invention can be produced, using any known reaction methods or according to any per-se known methods. The compounds (1) of the invention can be produced not only according to ordinary liquid-phase production methods but also according to any solid-phase methods such as combinatorial production methods or parallel production methods that are being significantly developed these days.

The compounds of the invention can be prepared, for example, according to the methods mentioned below.

Production Method 1

A compound of a general formula (IV):

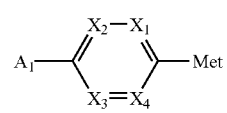

(IV)

[wherein Met represents an ordinary organic metal atom; $A_1$ represents a group of a formula (III-1-1):

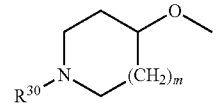

(III-1-1)

(wherein $R^{30}$ represents the above-mentioned $R^3$, or represents an amino-protective group; and the other symbols have the same meanings as above), or a group of a formula (III-2-1):

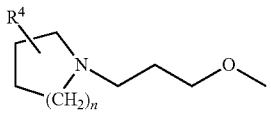
(III-2-1)

(wherein each symbols have the same meanings as above)]

is reacted with a compound of a formula (V):

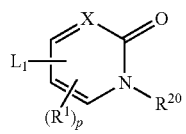
(V)

[wherein $L_1$ represents a leaving group; $R^{20}$ represents a group of the above-mentioned $R^2$, or a suitably protected $R^2$; and the other symbols have the same meanings as above]

in the presence of a catalyst, thereby giving a compound of a formula (I-A):

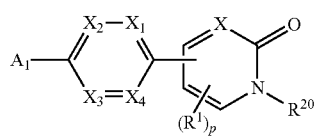
(I-A)

[wherein each symbols have the same meanings as above], and when $A_1$ has an amino-protective group, then the protective group is removed to give a compound of a formula (I-B) or its salt:

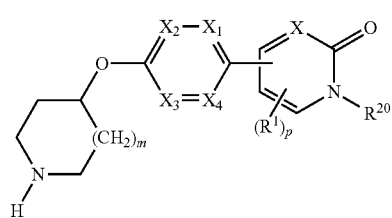
(I-B)

[wherein each symbols have the same meanings as above], and thereafter this is reacted with

$R^3$-$L_2$

[wherein $L_2$ represents a leaving group, and the other symbol has the same meaning as above] or

$R^3$=O

[wherein the symbol has the same meaning as above] to produce a compound of a formula (I):

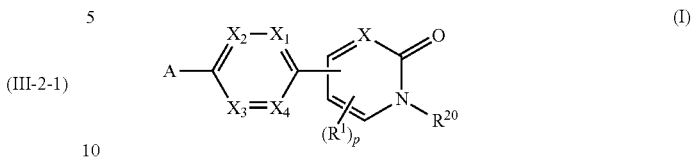
(I)

[wherein each symbols have the same meanings as above].

When $A_1$ in formula (I-A) does not have an amino-protective group, any other protective group may be optionally removed to produce the compound of formula (I).

The ordinary organic metal atom of Met means an organic metal atom generally used in cross-coupling reaction, including, for example, lithium, boron, silicon, magnesium, aluminium, zinc, tin, more preferably boron, zinc, tin. Regarding the concrete embodiments of its use, for example, boron may be used as boric acid or borates; zinc may be used as zinc chloride, zinc bromide or zinc iodide; and tin may be used as tri-lower alkyl-tin.

The leaving group for $L_1$ may be any one having the function of leaving in the reaction of the compounds of formulae (IV) and (V) to give the compound of formula (I-A). More concretely, $L_1$ includes, for example, a halogen atom such as a chlorine atom, a bromine atom or an iodine atom; an organic sulfonyl group such as a methanesulfonyl group, an ethanesulfonyl group, a benzenesulfonyl group; and an organic sulfonyloxy group such as a methanesulfonyloxy group, a trifluoromethanesulfonyloxy group, a p-toluenesulfonyloxy group et al.

$A_1$ represents a group of the above-mentioned A, or a suitably protected A. The protective group that may be introduced into A may be a protective group for amino group or hydroxyl group.

Not specifically defined, the protective group for amino group may be any one having its function. For example, preferred are an aralkyl group such as a benzyl group, a p-methoxybenzyl group, a 3,4-dimethoxybenzyl group, an o-nitrobenzyl group, a p-nitrobenzyl group, a benzhydryl group, a trityl group; a lower alkanoyl group such as a formyl group, an acetyl group, a propionyl group, a butyryl group, a pivaloyl group; a benzoyl group; an arylalkanoyl group such as a phenylacetyl group, a phenoxyacetyl group; a lower alkoxycarbonyl group such as a methoxycarbonyl group, an ethoxycarbonyl group, a propyloxycarbonyl group, a tert-butoxycarbonyl group; an aralkyloxycarbonyl group such as a benzyloxycarbonyl group, a p-nitrobenzyloxycarbonyl group, a phenethyloxycarbonyl group; a lower alkylsilyl group such as a trimethylsilyl group, a tert-butyldimethylsilyl group; a tetrahydropyranyl group; a trimethylsilylethoxymethyl group; a lower alkylsulfonyl group such as a methylsulfonyl group, an ethylsulfonyl group; an arylsulfonyl group such as a benzenesulfonyl group, a toluenesulfonyl group; and more preferred are an acetyl group, a benzoyl group, a tert-butoxycarbonyl group, a trimethylsilylethoxymethyl group, a methylsulfonyl group et al.

The protective group for hydroxyl group concretely includes, for example, a lower alkyl group such as a methyl group, an ethyl group, a propyl group, an isopropyl group, a tert-butyl group; a lower alkylsilyl group such as a trimethylsilyl group, a tert-butyldimethylsilyl group; a lower alkoxymethyl group such as a methoxymethyl group, a 2-methoxyethoxymethyl group; a tetrahydropyranyl group; a trimethylsilylethoxymethyl group; an aralkyl group such as a benzyl group, a p-methoxybenzyl group, a 2,3-dimethoxybenzyl group, an o-nitrobenzyl group, a p-nitrobenzyl group, a trityl group; an acyl group such as a formyl group, an acetyl group. Of those, preferred are a methyl group, a methoxymethyl group, a tetrahydropyranyl group, a trityl group, a trimethylsilylethoxymethyl group, a tert-butyldimethylsilyl group, an acetyl group et al.

The introduction and the removal of the protective group for amino group or hydroxyl group may be attained according to the methods described in references (e.g., *Protective Groups in Organic Synthesis*, written by T. W. Green, 2nd Ed., by John Wiley & Sons, 1991), or according to methods similar to these, or by combining these with any ordinary method.

$R^{20}$ represents a group of the above-mentioned R, or a suitably protected $R^2$. The protective group to be suitably introduced into $R^2$ may be a protective group for hydroxyl group.

The hydroxyl group-protective group concretely includes those mentioned hereinabove for the hydroxyl group-protective group that may be suitably introduced into A. The introduction and the removal of the protective group may be attained according to the methods described in references (e.g., *Protective Groups in Organic Synthesis*, written by T. W. Green, 2nd Ed., by John Wiley & Sons, 1991), or according to methods similar to these, or by combining these with any ordinary method.

The compounds of formulae (IV) and (V) may be used as commercially-available ones, or may be prepared in any known methods with commercially-available products, or according to such known methods, or according to the methods described in Examples and Reference Examples given hereinunder, optionally suitably combining them.

The compound of formula (IV) concretely includes, for example, 4-(1-t-butoxycarbonylpiperidin-4-yloxy)phenylboronic acid, 4-(4,4,5,5-tetramethyl-1,3,2-dioxaboran-2-yl)phenoxy-1-t-butoxycarbonylpiperidine, 4-(4,4,5,5-tetramethyl-1,3,2-dioxaboran-2-yl)phenoxy-1-cyclopropylpiperidine, 4-(4,4,5,5-tetramethyl-1,3,2-dioxaboran-2-yl)phenoxy-1-isopropylpiperidine, 4-(4,4,5,5-tetramethyl-1,3,2-dioxaboran-2-yl)phenoxy-1-cyclobutylpiperidine, 4-(4,4,5,5-tetramethyl-1,3,2-dioxaboran-2-yl)phenoxy-1-cyclopentylpiperidine, 4-(4-trimethylstannylphenoxy)-1-t-butoxycarbonylpiperidine, 4-(4-tributylstannylphenoxy)-1-t-butoxycarbonylpiperidine et al.

The compound of formula (V) concretely includes, for example, 5-bromo-1-methyl-2(1H)-pyridone, 5-bromo-1-(difluoromethyl)-2(1H)-pyridone, 4-iodo-1-(difluoromethyl)-2(1H)-pyridone, 5-bromo-1,3-dimethyl-2(1H)-pyridone, 5-bromo-1-methoxy-2(1H)-pyridone, 3-bromo-1-methyl-2(1H)-pyridone, 6-bromo-1-methyl-2(1H)-pyridone, 5-bromo-3-chloro-1-methyl-2(1H)-pyridone, 3,5-dichloro-1-methyl-2(1H)-pyridone, 5-bromo-1 methyl-2(1H)-pyrimidone, 5-bromo-1-ethyl-2(1H)-pyridone, 5-bromo-1-isopropyl-2(1H)-pyridone, 5-bromo-1-ethoxy-2(1H)-pyridone, 5-bromo-1-isopropoxy-2(1H)-pyridone.

The reaction of the compound of formula (IV) with the compound of formula (V) may be attained, generally using from 0.5 to 5 mols, preferably from 0.7 mols to 3 mols of the compound (V) relative to one mol of the compound (IV).

The catalyst to be used in the reaction may be a transition metal generally used in cross-coupling reaction, such as copper, nickel, palladium et al. More concretely, preferred are tetrakis(triphenylphosphine)palladium(0), palladium(II)acetate, bis(triphenylphosphine)palladium(II) chloride, [1,1'-bis(diphenylphosphino)ferrocene]palladium(II)dichloride et al.

The reaction may be effected generally in an inert solvent. The insert solvent is, for example, preferably water, benzene, toluene, xylene, methylene chloride, chloroform, dimethoxyethane, tetrahydrofuran, dioxane, dimethylformamide et al, or their mixed solvent.

The reaction temperature may be generally from room temperature to the boiling point of the solvent used in the reaction, preferably from 20° C. to 200° C.

The reaction time may be generally from 30 minutes to 7 days, preferably from 3 hours to 2 days.

The reaction is preferably effected in the presence of a base, and the base includes, for example, inorganic bases such as sodium hydroxide, potassium hydroxide, sodium hydrogencarbonate, sodium carbonate, potassium carbonate, cesium carbonate et al; and organic bases such as triethylamine, diisopropylamine et al.

The amount of the base to be used may be generally from 0.5 mols to 5 mols, preferably from 0.7 mols to 3 mols relative to one mol of the compound of formula (VI).

After the reaction, when the product does not have an amino-protective group, then any other protective group is optionally removed, and thereafter the product may be isolated and purified through any ordinary isolation and purification method of, for example, concentration, concentration under reduced pressure, reprecipitation, solvent extraction, crystallization, chromatography et al.

The reaction of the compound or its salt of formula (1-B) with the compound $R^3$-$L_2$ may be attained, generally using from 0.5 mols to 5 mols, preferably from 0.7 mols to 3 mols of the compound $R^3$-$L_2$ relative to one mol of the compound (1-B).

The reaction may be effected generally in an inert solvent. The insert solvent is, for example, preferably water, methanol, ethanol, benzene, toluene, xylene, methylene chloride, chloroform, dimethoxyethane, tetrahydrofuran, dioxane, dimethylformamide, or their mixed solvent.

The reaction temperature may be generally from room temperature to the boiling point of the solvent used in the reaction, preferably from 20° C. to 150° C.

The reaction time may be generally from 30 minutes to 7 days, preferably from 3 hours to 2 days.

The reaction is preferably effected in the presence of a base, and the base includes, for example, inorganic bases such as sodium hydroxide, potassium hydroxide, sodium hydrogencarbonate, sodium carbonate, potassium carbonate, cesium carbonate et al; and organic bases such as triethylamine, diisopropylamine et al.

The amount of the base to be used may be generally from 1 mol to 5 mols, preferably from 1 mol to 3 mols relative to one mol of the compound of formula (1-B).

The reductive alkylation of the compound or its salt of formula (1-B) with the compound $R^3$=O may be attained, generally using from 1 mol to 7 mols, preferably from 2 mols to 4 mols of the compound $R^3$-$L_2$ relative to one mol of the compound (1-B).

The reducing agent to be used in the reaction may be an organic metal reagent such as sodium borohydride, sodium cyanoborohydride, sodium triacetoxyborohydride et al.

The amount of the reducing agent to be used may be generally from 1 mol to 5 mols, preferably from 1 mol to 3 mols relative to one mol of the compound of formula (1-B).

The reaction may be effected generally in an inert solvent. The insert solvent is, for example, preferably methanol, ethanol, benzene, toluene, xylene, methylene chloride, chloroform, dimethoxyethane, tetrahydrofuran, dioxane, dimethylformamide, or their mixed solvent.

The reaction temperature may be generally from room temperature to the boiling point of the solvent used in the reaction, preferably from 20° C. to 100° C.

The reaction time may be generally from 30 minutes to 7 days, preferably from 3 hours to 2 days.

After the reaction, any other protective group is optionally removed, and thereafter the product may be isolated and purified through any ordinary isolation and purification method of, for example, concentration, concentration under reduced pressure, reprecipitation, solvent extraction, crystallization, chromatography et al.

Compounds of formula (I-1') which is within the scope of formula (I) may be prepared, for example, according to the following method.

Production Method 2

A compound of formula (IV-2):

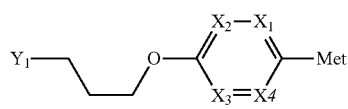

(IV-2)

[wherein $Y_1$ represents a hydroxyl group, a protected hydroxyl group, or a halogen atom; and the other symbols have the same meanings as above] is reacted with a compound of formula (V):

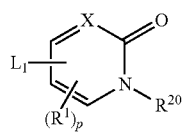

(V)

[wherein each symbols have the same meanings as above] in the presence of a catalyst, thereby giving a compound of formula (I-A):

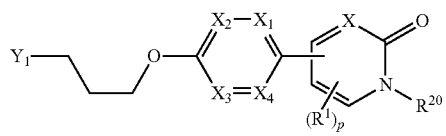

(I-A)

[wherein each symbols have the same meanings as above], and optionally $Y_1$ is converted into a leaving group, and thereafter the compound of formula (I-A) or the compound of formula (I-A) where $Y_1$ has been converted into a leaving group, is reacted with a compound of formula (VI):

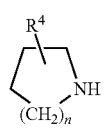

(VI)

[wherein each symbols have the same meanings as above], and optionally the protective group is removed to thereby produce a compound of:

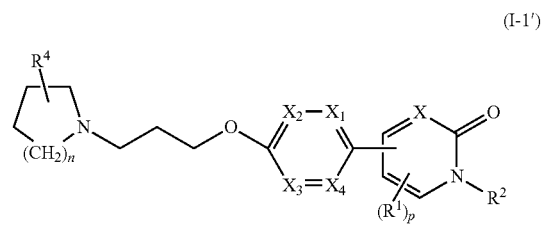

(I-1')

[wherein each symbols have the same meanings as above].

The reaction of the compound of formula (IV-2) with the compound of formula (V-2) may be attained, generally using from 0.5 mols to 5 mols, preferably from 0.7 to 3 mols of the compound (V-2) relative to one mol of the compound (IV-2).

The catalyst to be used in the reaction may be a transition metal generally used in cross-coupling reaction, such as copper, nickel, palladium et al. More concretely, preferred are tetrakis(triphenylphosphine)palladium(0), palladium(II)acetate, bis(triphenylphosphine)palladium(II) chloride, [1,1'-bis(diphenylphosphino)ferrocene]palladium(II)dichloride et al.

The reaction may be effected generally in an inert solvent. The insert solvent is, for example, preferably water, benzene, toluene, xylene, methylene chloride, chloroform, dimethoxyethane, tetrahydrofuran, dioxane, dimethylformamide et al, or their mixed solvent.

The reaction temperature may be generally from room temperature to the boiling point of the solvent used in the reaction, preferably from 20° C. to 200° C.

The reaction time may be generally from 30 minutes to 7 days, preferably from 3 hours to 2 days.

The reaction is preferably effected in the presence of a base, and the base includes, for example, inorganic bases such as sodium hydroxide, potassium hydroxide, sodium hydrogencarbonate, sodium carbonate, potassium carbonate, cesium carbonate; and organic bases such as triethylamine, diisopropylethylamine et al.

The amount of the base to be used may be generally from 0.5 mols to 5 mols, preferably from 0.7 mols to 3 mols relative to one mol of the compound of formula (IV-2).

After the reaction, when the product has a protective group, then the protective group is removed prior to its isolation and purification, but when the product does not have a protective group, the product may be directly isolated and purified through any ordinary isolation and purification method of, for example, concentration, concentration under reduced pressure, reprecipitation, solvent extraction, crystallization, chromatography et al.

The introduction and the removal of the protective group may be attained according to the method described in the reference as in Production Method 1, or according to methods similar to it, or by combining it with any ordinary method.

The compound of (IV-2) may be used as commercially-available ones, or may be prepared in any known methods with commercially-available products, or according to such known methods, or according to the methods described in Examples and Reference Examples given hereinunder, optionally suitably combining them.

The compound of formula (IV-2) concretely includes, for example, 4-(3-chloropropoxy)phenylboronic acid, 3-chloro-1-(4-(4,4,5,5-tetramethyl-1,3,2-dioxaboran-2-yl)phenoxy)

propane, 3-acetoxy-1-(4-(4,4,5,5-tetramethyl-1,3,2-dioxaboran-2-yl)phenoxy)propane, 3-t-butyldimethylsiloxy-1-(4-(4,4,5,5-tetramethyl-1,3,2-dioxaboran-2-yl)phenoxy)propane, 3-(4-tributylstannylphenoxy)-1-chloropropane, 3-(4-trimethylstannylphenoxy)-1-chloropropane et al.

The compound of formula (V) includes the same as those of formula (V) in Production Method 1.

The compound of formula (VI):

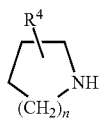
(VI)

[wherein each symbols have the same meanings as above] includes, for example, azetidine, 2-methylazetidine, 3-methylazetidine, pyrrolidine, 2-methylpyrrolidine, 3-methylpyrrolidine, piperidine, 2-methylpiperidine, 3-methylpiperidine, 4-methylpiperidine, 2-ethylazetidine, 3-ethylazetidine, 2-ethylpyrrolidine, 3-ethylpyrrolidine, 2-ethylpiperidine, 3-ethylpiperidine, 4-ethylpiperidine et al.

The leaving group to be converted from $Y_1$ in formula (VI) includes, for example, a halogen atom such as a chlorine atom, a bromine atom or an iodine atom; an organic sulfonyloxy group such as a methanesulfonyloxy group, an ethanesulfonyloxy group, a trifluoromethanesulfonyloxy group, a p-toluenesulfonyloxy group et al.

$Y_1$ in formula (VI) may be converted into the leaving group according to the methods described in references (e.g., *Comprehensive Organic Synthesis*, Vol. 6, Pergamon Press, 1991; *Comprehensive Organic Transformations*, Richard L. et al., VCH Publishers, 1988), or according to methods similar to these, or by combining these with any ordinary method. Concretely, for example, using methanesulfonyl chloride, ethanesulfonyl chloride, p-toluenesulfonyl chloride or trifluoromethanesulfonyl chloride in the presence of a base, a hydroxyl group may be converted into a methanesulfonyloxy group, an ethanesulfonyloxy group, a p-toluenesulfonyloxy group or a trifluoromethanesulfonyloxy group, respectively.

Compounds of formula (I-2):

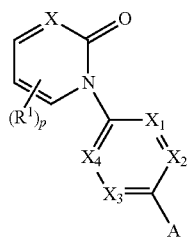
(I-2)

[wherein each symbols have the same meanings as above] which is within the scope of formula (I) may be produced, for example, according to the following method.

Production Method 3

A compound of formula (IV):

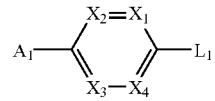
(IV)

[wherein each symbols have the same meanings as above] is reacted with a compound of formula (V-3):

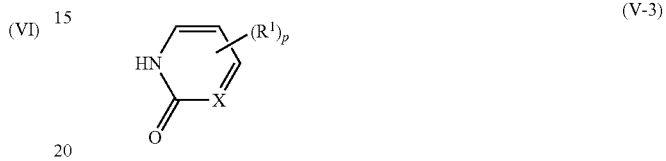
(V-3)

[wherein each symbols have the same meanings as above] in the presence of a base, thereby giving a compound of formula (I-20):

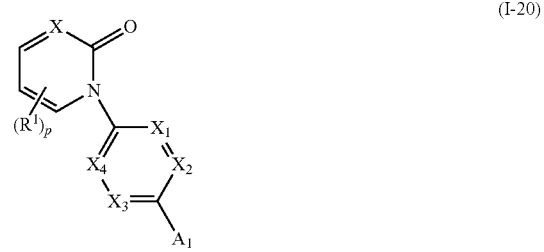
(I-20)

[wherein each symbols have the same meanings as above], and optionally the protective group is removed, thereby producing a compound of formula (I-2):

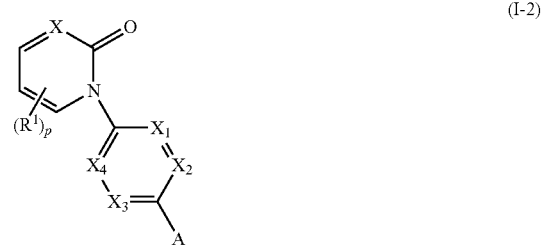
(I-2)

[wherein the symbols have the same meanings as above].

The reaction of the compounds of formulae (IV) and (V-3) may be attained, generally using from 1 mol to 5 mols, preferably from 1.5 mols to 3 mols of the compound (IV) relative to one mol of the compound (V-3).

This reaction is preferably effected in the presence of copper iodide. The amount of copper iodide to be used may be generally from 0.005 mols to 0.5 mols, preferably from 0.01 mols to 0.2 mols relative to 1 equivalent of the compound (IV).

The reaction may be effected generally in an inert solvent. The inert solvent is, for example, preferably water, benzene, toluene, xylene, methylene chloride, chloroform, dimethoxyethane, tetrahydrofuran, dioxane, dimethylformamide et al, or their mixed solvent.

The reaction temperature may be generally from room temperature to the boiling point of solvent used in the reaction, preferably from 20° C. to 200° C.

The reaction time may be generally from 30 minutes to 7 days, preferably from 3 hours to 2 days.

After the reaction, when the product has a protective group, then the protective group is removed prior to its isolation and purification, but when the product does not have a protective group, the product may be directly isolated and purified through any ordinary isolation and purification method of, for example, concentration, concentration under reduced pressure, reprecipitation, solvent extraction, crystallization, chromatography et al.

The introduction and the removal of the protective group may be attained according to the method described in the reference as in Production Method 1, or according to methods similar to these, or by combining these with any ordinary method.

These compounds may be converted into pharmaceutically-acceptable salts or esters in any ordinary manner; and on the contrary, such salts or esters may be converted into the corresponding free compounds in any ordinary manner.

The substituted pyridone derivatives of the invention may form their pharmaceutically-acceptable salts. The compounds of formula (I), and the compounds of formula (I-1), (I-1') or (I-2) which are within the scope of formula (I) may be converted into their salts in any ordinary manner. The acid addition salts include, for example, hydrohalides such as hydrochlorides, hydrofluorides, hydrobromides, hydroiodides; inorganic acid salts such as nitrates, perchlorates, sulfates, phosphates, carbonates et al; lower alkylsulfonates such as methanesulfonates, trifluoromethanesulfonates, ethanesulfonates et al; arylsulfonates such as benzenesulfonates, p-toluenesulfonates et al; organic acid salts such as fumarates, succinates, citrates, tartrates, oxalates, maleates et al; amino acid salts such as glutamates, aspartates et al.

The base addition salts include, for example, alkali metal salts with sodium, potassium, et al; alkaline earth metal salts with calcium, magnesium et al; ammonium salts; organic bases with guanidine, triethylamine, dicyclohexylamine et al. Further, the compounds of the invention may be in any form of hydrates or solvates of their free compounds or salts.

The compounds of formula (I) and their pharmaceutically-acceptable salts may be administered orally or parenterally.

In clinical use of the compounds of the invention, pharmaceutically-acceptable additives may be added thereto to formulate various preparations in accordance with the intended administration route thereof. Various additives commonly used in the field of pharmaceutical compositions may be used herein, including, for example, gelatin, lactose, white sugar, titanium oxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, hydroxypropylcyclodextrin et al.

Combined with such additives, the compound of the invention may be formulated into solid preparations (e.g., tablets, capsules, granules, powders and suppositories) and liquid preparations (e.g., syrups, elixirs, injections). These preparations can be produced in any method known in the field of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto. The preparations may contain the compound of the invention in an amount of from 1.0 to 100% by weight, preferably from 1.0 to 60% by weight of the preparation.

The compounds of the invention may be formulated into preparations, for example, according to the following Formulation Examples.

Formulation Example 1

10 parts of the compound of Example 1 to be described hereinunder, 15 parts of heavy magnesium oxide and 75 parts of lactose are uniformly mixed to prepare a powdery or granular preparation having a particle size of at most 350 µm. The preparation is encapsulated to give capsules.

Formulation Example 2

45 parts of the compound of Example 1 to be described hereinunder, 15 parts of starch, 16 parts of lactose, 21 parts of crystalline cellulose, 3 parts of polyvinyl alcohol and 30 parts of distilled water are uniformly mixed, then ground, granulated and dried, and then sieved to give a granular preparation having a particle diameter of from 1410 to 177 µm.

Formulation Example 3

A granular preparation is prepared in the same manner as in Formulation Example 2. 96 parts of the granular preparation is mixed with 3 parts of calcium stearate, and shaped under compression into tablets having a diameter of 10 mm.

Formulation Example 4

90 parts of the granular preparation obtained according to the method of Formulation Example 2 is mixed with 10 parts of crystalline cellulose and 3 parts of calcium stearate, and shaped under compression into tablets having a diameter of 8 mm. These are coated with a mixed suspension of syrup gelatin and precipitated calcium carbonate to give sugar-coated tablets.

These preparations may contain any other therapeutically-effective drug, as described below.

In their use, the compounds of the invention may be combined with any other drug effective for treatment (prevention or therapy) of metabolic disorders or dietary disorders. The individual ingredients to be combined may be administered at different times or at the same time, either as one preparation or as divided different preparations. The combination of the compound of the invention with any other drug effective for treatment of metabolic disorders or dietary disorders includes, in principle, combinations thereof with any drug effective for treatment of metabolic disorders or dietary disorders.

The compounds of the invention may also be combined with any other drug effective for hypertension, obesity-related hypertension, hypertension-related disorders, cardiomegaly, left ventricle hypertrophy, metabolic disorders, obesity, obesity-related disorders (these are hereinafter referred to as "co-drugs"). Such co-rugs may be administered at the same time or at different times or successively in order in prevention or treatment of the above-mentioned disorders. When the compound of the invention is used simultaneously with one or more co-drugs, it may be in a pharmaceutical composition for one-dose administration. However, in such combination therapy, the composition containing the compound of the invention and the co-drug may be administered to subjects simultaneously, or separately or successively. The composition and the co-drug may be packed separately. They may be administered at different times.

The dose of the co-drug may depend on the clinical use thereof, and may be suitably determined in accordance with the administration subject, the administration route, the diseases and the combination. The form of the co-drug for administration is not specifically defined, and it may be combined with the compound of the invention when they are administered. The administration mode includes, for example, the following: (1) A compound of the invention is combined with a co-rug to give a single preparation for single administration; (2) a compound of the invention and a co-drug are separately formulated into different two preparations, and the two preparations are simultaneously administered in one administration route; (3) a compound of the invention and a co-drug are separately formulated into different two preparations, and they are administered at different times in one and the same administration route; (4) a compound of the invention and a co-rug are separately formulated into different two preparations, and they are administered at the same time in two different administration routes; (5) a compound of the invention and a co-drug are separately formulated into different two preparations, and they are administered at different times in different administration routes (for example, a compound of the invention and a co-drug are administered in that order, or in an order contrary to this). The blend ratio of the compound of the invention and the co-drug may be suitably determined depending on the administration subject, the administration route, and the disease for the administration.

The co-drugs usable in the invention include remedy for diabetes, remedy for hyperlipemia, remedy for hypertension, and anti-obesity drugs et al. Two or more co-drugs may be combined in any desired ratio.

The remedy for diabetes includes, for example, the following:
1) PPAR (peroxisome proliferator-activated receptor)-γ agonists such as glitazones (e.g., ciglitazone, darglitazone, englitazone, isaglitazone (MCC-555), pioglitazone, rosiglitazone, troglitazone, BRL49653, CLX-0921, 5-BTZD), GW-0207, LG-100641, LY-300512 et al;
2) biguanides such as metformin, buformin, phenformin et al;
3) protein tyrosine phosphatase 1B inhibitors;
4) sulfonylureas such as acetohexamide, chloropropamide, diabinese, glibenclamide, glipizide, glyburide, glimepiride, glicilazide, glipentide, gliquidone, glisolamide, trazamide, tolubutamide et al;
5) meglitinides such as repaglinide, nateglinide et al;
6) α-glucoside hydrolase inhibitors such as acarbose, adiposine, camiglibose, emiglitate, miglitol, voglibose, pradimicin-Q, salbostatin, CKD-711, MDL-25,673, MDL-73,945, MOR14 et al;
7) α-amylase inhibitors such as tendamistat, trestatin, A13688 et al;
8) insulin secretion promoters such as linogliride, AA4166 et al;
9) fatty acid oxidation inhibitors such as clomoxir, etomoxir et al;
10) A2 antagonists such as midaglizole, isaglidole, deriglidole, idazoxan, earoxan, fluparoxan;
11) insulin or insulin mimetics such as biota, LP-100, novalapid, insulin determir, insulin lispro, insulin glargine, insulin zinc, Lys-Pro-insulin, GLP-1 (73-7), GLP1 (7-36)-$NH_2$ et al;
12) non-thiazolidinediones such as JT-501, farglitazar et al;
13) PPARα/γ dual-agonists such as CLX-0940, GW-1536, GW-1929, GW-2433, KPR-297, L-796449, L-90 and SB219994;
14) other insulin sensitizes, and
15) VPAC2 receptor agonists.

The remedy for hyperlipemia include, for example, the following:
1) bile acid absorption promoters such as cholesterylamine, colesevelem, colestipol, dialkylaminoalkyl derivatives of crosslinked dextran, Colestid®, LoCholest®, Questran® et al;
2) HMG-CoA reductase inhibitors such as atorvastatin, itavastatin, fluvastatin, lovastatin, pravastatin, rivastatin, rosuvastatin, simvastatin, ZD-4522 et al;
3) HMG-CoA synthase inhibitors;
4) cholesterol absorption inhibitors such as snatol ester, β-sitosterol, sterol glucoside, ezetimibe et al;
5) ACAT (acyl-CoA-cholesterol acyltransacylase) inhibitors such as avasimibe, eflucimibe, KY-505, SMP-709 et al;
6) CETP inhibitors such as JTT705, torcetrapib, CP532632, BAY-63-2149, SC-591, SC-795 et al;
7) squalane synthetase inhibitors;
8) antioxidants such as probucol;
9) PPARα agonists such as beclofibrate, benzafibrate, syprofibrate, clofibrate, etofibrate, fenofibrate, gemcabene, gemfibrozil, GW-7647, BM-170744, LY-518674, fibric acid derivatives (e.g., Atromid®, Lopid®, Tricor®) et al;
10) FXR receptor antagonists such as GW-4064, SR-103912 et al;
11) LXR receptor agonists such as GW3965, T9013137, XTCO-179628 et al;
12) lipoprotein synthesis inhibitors such as niacin;
13) renin-angiotensin system inhibitors;
14) PPARδ partial agonists;
15) bile acid resorption inhibitors such as BARA1453, SC435, PHA384640, S-435, AZD7706 et al;
16) PPARδ agonists such as GW501516, GW590735;
17) triglyceride synthesis inhibitors;
18) MTTP (microsomic triglyceride transportation) inhibitors such as inplitapide, LAB687, CP346086;
19) transcription modifying factors;
20) squalane epoxidase inhibitors;
21) LDL (low-density lipoprotein) receptor derivatives,
22) platelet agglutination inhibitors;
23) 5-LO (5-lipoxygenase)/FLAP (5-lipoxygenase activated protein) inhibitors; and
24) niacin receptor agonists.

The remedy for hypertension include, for example, the following:
1) thiazide diuretics such as chlorothialidon, chlorothiazide, dichlorofenamide, hydrofluorothiazide, indapamide, hydrochlorothiazide et al; loop diuretics such as bumetanide, ethacrynic acid, flosemide, tolusemide et al; sodium diuretics such as amyloride, triamuteren et al; aldosterone antagonist diuretics such as spironolactone, epilenone et al;
2) β-adrenaline blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, probanolol, sotalol, tartatolol, tilisolol, timolol et al;
3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, verapamil et al;

4) angiotensin converting enzyme inhibitors such as benazepril, captopril, cilazapril, delapril, enalapril, fosinopril, imidapril, losinopril, moexipril, quinapril, quinaprilat, ramipril, perindopril, perindoropril, quanipril, spirapril, tenocapril, trandolapril, zofenopril et al;

5) neutral endopeptidase inhibitors such as omapatrilat, cadoxatril, ecadotril, fosidotril, sampatrilat, AVE7688, ER4030 et al;

6) endothelin antagonists such as tezosentan, A308165, YM62899 et al;

7) vasodilators such as hydraladine, clonidine, minoxidil, nicotinyl alcohol et al;

8) angiotensin II receptor antagonists such as candesartan, eprosartan, iribesartan, losartane, pratosartan, tasosartan, telmisartan, valsartan, EXP-3137, FI6828K, RNH6270 et al;

9) α/β adrenalin blockers such as nipradilol, arotinolol, amoslalol et al;

10) α1 blockers such as terazosin, urapidil, prazosin, bunazosin, trimazosin, doxazosin, naphthopidil, indolamin, WHIP164, XEN010 et al;

11) α2 agonists such as lofexidine, tiamenidine, moxonidine, rilmenidine, guanobenz; and 12) aldosterone inhibitors.

The anti-obesity drugs include, for example, the following:

1) 5HT (serotonin) transporter inhibitors such as paroxetine, fluoxetine, fenfluramine, fluvoxamine, sertraline, imipramine et al;

2) NE (norepinephrine) transporter inhibitors such as GW320659, desipramine, talsupramin, nomifensin et al;

3) CB-1 (cannabinoid-1 receptor) antagonists/inverse-agonists such as limonabant (Sanofi Synthelabo), SR-147778 (Sanofi Synthelabo), BAY-65-2520 (Bayer), SLV-319 (Sorbei), as well as compounds disclosed in U.S. Pat. No. 5,532, 237, U.S. Pat. No. 4,973,587, U.S. Pat. No. 5,013,837, U.S. Pat. No. 5,081,122, U.S. Pat. No. 5,112,820, U.S. Pat. No. 5,292,736, U.S. Pat. No. 5,624,941, U.S. Pat. No. 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887 and EP-658546;

4) glerin antagonists such as compounds disclosed in WO01/87355, WO02/08250 et al;

5) histamine (H3) antagonists/inverse-agonists such as thioperamide, 3-(1H-imidazol-4-yl)propyl N-(pentenyl)carbonate, clobenpropit, iodofenpropit, imoproxyfen, GT2395, A331440, compounds disclosed in WO02/15905, O-[3-(1H-imidazol-4-yl)propanol]carbamate, piperazine-containing H3-receptor antagonists (Lazewska, D. et al., *Pharmazie*, 56: 927-32 (2001)), benzophenone derivatives Sasse, A. et al., *Arch. Pharm.* (Weinheim) 334: 45-52 (2001)), substituted N-phenylcarbamates (Reidemeister, S. et al., *Pharmazie*, 55: 83-6 (2000)), proxyfen derivatives (Sasse, A. et al., *J. Med. Chem.*, 43: 3335-43 (2000)) et al;

6) MCH-1R (melamine concentrating hormone receptor 1) antagonists such as T-226296 (Takeda), SNP-7941 (Synaptic), other compounds disclosed in WO01/82925, WO01/87834, WO02/051809, WO02/06245, WO02/076929, WO02/076947, WO02/04433, WO02/51809, WO02/083134, WO02/094799, WO03/004027 and JP-A 2001-226269;

7) MCH-2R (melamine concentrating hormone receptor 2) agonists/antagonists;

8) NPY1 (neuropeptide Y1) antagonists such as BIBP3226, J-115814, BIBO3304, LY-357897, CP-671906, GI-264879, and other compounds disclosed in U.S. Pat. No. 6,001,836, WO96/14307, WO01/23387, WO99/51600, WO01/85690, WO01/85098, WO01/85173 and WO01/89528;

9) NPY5 (neuropeptide Y5) antagonists such as 152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. No. 6,140,354, U.S. Pat. No. 6,191,160, U.S. Pat. No. 6,258,837, U.S. Pat. No. 6,313,298, U.S. Pat. No. 6,337,332, U.S. Pat. No. 6,329,395, U.S. Pat. No. 340, 683, U.S. Pat. No. 6,326,375, U.S. Pat. No. 6,329,395, U.S. Pat. No. 6,337,332, U.S. Pat. No. 6,335,345, EP-01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO1/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789, and compounds disclosed in Norman et al., *J. Med. Chem.*, 43:4288-4312 (2000) et al;

10) reptins such as human recombinant reptin (PEG-OB, Hoffman La Roche), recombinant methionylreptin (Amgen);

11) reptin derivatives such as compounds disclosed in U.S. Pat. No. 5,552,524, U.S. Pat. No. 5,552,523, U.S. Pat. No. 5,552,522, U.S. Pat. No. 5,521,283, WO96/23513, WO96/23514, WO96/23515, WO96/23516, WO96/23517, 96/23518, WO96/23519 and WO96/23520;

12) opioid antagonists such as narmefen (Revex®), 3-methoxynartorexon, naloxone, nartolexon, compounds disclosed in WO00/21509;

13) aurexin antagonists such as SB-334867A, and other compounds disclosed in WO01/96302, WO01/68609, WO02/51232, WO02/51838, WO03/023561;

14) BRS3 (bonbesin receptor subtype-3) agonists;

15) CCK-A (cholecystokinin A) agonists such as AR-R15849, GI-181771, JMV-180, A-71378, A-71623, SR-146131, and other compounds disclosed in U.S. Pat. No. 5,739,106;

16) CNTF (ciliary neurotrophic factors) such as GI-181771 (Glaxo-Smith Kline), SR-146131 (Sanofi Synthelabo), butabindide, PD170,292, PD149164 (Pfizer) et al;

17) CNTF derivatives such as axokine (Regeneron), and other compounds disclosed in WO94/09134, WO98/22128, WO99/43813 et al;

18) GHS (growth hormone secretion promoter receptor) agonists such as NN703, hexarelin, MK-0677, SM-130686, CP-424,391, L-692,429, L-163,255, and compounds disclosed in U.S. Pat. No. 6,358,951, US Patent Application Nos. 2002/049196, 2002/022637, WO01/56592, WO02/32888 et al;

19) 5HT2c (serotonin receptor-2c) agonists such as BVT933, DPCA37215, IK264, PNU22394, WAY161503, R-1065, YM348, and other compounds disclosed in U.S. Pat. No. 3,914,250, WO02/36596, WO02/48124, WO02/10169, WO01/66548, WO02/44152, WO02/51844, WO02/40456 and WO02/40457;

20) Mc3r (melanocortin-3 receptor) agonists;

21) Mc4r (melanocortin-4 receptor) agonists such as CHIR86036 (Chiron), ME-10142, ME-10145 (Melacure), and other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/

068388, WO02/067869, WO03/007949 and WO03/009847;
22) monoamine re-uptake inhibitors such as sibutramine (Meridia®/Recuctil®) and its salts, and other derivatives disclosed in U.S. Pat. No. 4,746,680, U.S. Pat. No. 4,806,570, U.S. Pat. No. 5,436,272, US Patent Application No. 2002/0006964, WO01/27068 and WO01/62341; 23) serotonin re-uptake inhibitors such as dexfenfluramine, fluoxetine, and other compounds disclosed in U.S. Pat. No. 6,365,633, WO01/27060 and WO01/162341;
24) GLP1 (glucagon-like peptide-1) agonists;
25) topiramate (Topimax®);
26) phytopharm compound 57 (e.g., CP644,673);
27) ACC2 (acetyl CoA carboxylase-2) inhibitors;
28) β3 (adrenalin receptor-3) agonists such as AD9677/TAK677 (Dai-Nippon Pharmaceutical/Takeda Chemical), CL-316,243, SB418790, BRL-37344, L-796568, BMS-196085, BRL-35135A, CGP12177A, BTA-243, W427353, trecadrine, Zeneca D7114, SR59119A, and other compounds disclosed in U.S. Pat. No. 5,705,515, U.S. Pat. No. 5,451,677, WO01/74782 and WO02/32897;
29) DGAT1 (diacylglycerol acyltransferase-1) inhibitors;
30) DGAT2 (diacylglycerol acyltransferase-2) inhibitors,
31) FAS (fatty acid synthase) inhibitors such as cerulenin, C75;
32) PDE (phosphodiesterase) inhibitors such as theophylline, pentoxifylline zaprinast, sildenafil, aminone, milrinone, cilostamide, rolipram and cilomilast;
33) thyroid hormone-β agonists such as KB-2611 (KaroBio BMS), and other compounds disclosed in WO02/15845, JP-A 2000-256190 et al;
34) UCP (uncoupling protein)-1, 2, or 3 activators such as phytanic acid, 4-[(E)-2-(5,6,7,8-tetrahydro-5,5,8,8-tetramethyl-2-naphthalenyl-1-propenyl]benzoic acid (TTNPB), retinoic acid, and other compounds disclosed in WO99/00123;
35) acylestrogens such as oleoylestrone (disclosed in del Mar-Grasa, M. et al., *Obesity Research*, 9:202-9 (2001)),
36) glucocorticoid antagonists;
37) 11-β HSD1 (11-β-hydroxysteroid dehydrogenase-1) inhibitors such as BVT3498, BVT2733, and other compounds disclosed in WO01/90091, WO01/90090, WO01/90092 et al;
38) SCD1 (stearoyl-CoA desaturase-1) inhibitors;
39) DP-IV (dipeptidyl peptidase-IV) inhibitors such as isoleucine thiazolidine, valine pyrrolidide, NVP-DPP728, AF237, P93/01, TSL225, TMC-2A/2B/2C, FE999011, P9310/K364, VIP0177, SDZ274444, and other compounds disclosed in WO03/004498, WO03/004496, EP1258476, WO02/083128, WO02/062764, WO03/000250, WO03/002530, WO03/002531, WO03/002553, WO03/002593, WO03/000180 and WO03/000181;
40) lipase inhibitors such as tetrahydroliptatin (Orlistat/Xenical®), Triton WR1339, RHC80267, lipstatin, tea saponin, diethylumbelliferyl phosphate, FL-386, WAY-121898, Bay-N-3176, valilactone, esteracin, ebelactone A, ebelactone B, RHC80267, and other compounds disclosed in WO01/77094, U.S. Pat. No. 4,598,089, U.S. Pat. No. 4,452,813, U.S. Pat. No. 5,512,565, U.S. Pat. No. 5,391,571, U.S. Pat. No. 5,602, 151, U.S. Pat. No. 4,405,644, U.S. Pat. No. 4,189,438 and U.S. Pat. No. 4,242,453;
41) fatty acid transporter inhibitors;
42) dicarboxylate transporter inhibitors;
43) glucose transporter inhibitors;
44) phosphate transporter inhibitors;
45) melanocortin agonists such as melanotan II, and other compounds disclosed in WO99/64002 and WO00/746799;
46) melanin concentrating hormone antagonists;
47) galanin antagonists;
48) CCK antagonists;
49) corticotropin release hormones;
50) PDE3 (phosphodiesterase 3B) agonists.

The compounds of the invention may be combined with one or more of the above-mentioned co-drugs. The combination of the compound of the invention with one or more co-rugs selected from a group consisting of remedy for diabetes and remedy for hyperlipemia is useful for prevention or remedy of metabolic disorders. In particular, a combination of the compound of the invention with a remedy for hypertension and an anti-obesity drug along with a remedy for diabetes or a drug for hyperlipemia is useful for prevention or remedy of metabolic disorders owing to the synergistic effect thereof.

When the compounds of the invention are used in clinical sites, the dose and the administration frequency thereof may vary depending on the sex, the age, the body weight and the condition of the patient and on the type and the scope of the treatment of the patient. In oral administration, in general, the dose may be from 0.01 to 100 mg/kg-adult/day, preferably from 0.03 to 1 mg/kg-adult/day, and it may be administered all at a time or may be administered in a few times as divided into a few portions. In parenteral administration, its dose may be from 0.001 to 10 mg/kg-adult/day, preferably from 0.001 to 0.1 mg/kg-adult/day, and it may be administered all at a time or may be administered in a few times as divided into a few portions.

Ordinary physicians, veterinarians and clinicians may readily determine the effective dose necessary for retarding, inhibiting or stopping the development of diseases.

EXAMPLES

The invention is described more concretely with reference to the following Examples, although the present invention is not limited at all by these Examples.

For the thin-layer chromatography of the compounds in the Examples, used was a plate of Silicagel 60F$_{245}$ (Merck); and for detection, used was a UV detector. Wakogel™ C-300 (Wako Pure Chemicals) was used for the column silica gel; and LC-SORB™ SP-B-ODS (Chemco) or YMC-GEL™ ODS-AQ 120-S50 (Yamamura Chemical Laboratories) was for the reversed-phase column silica gel. Mass spectrum was determined according to an electrospray ionization (ESI) process, using QuattroII (Micromass).

In NMR spectrometry, dimethyl sulfoxide was used for the internal standard in measurement in a heavy dimethyl sulfoxide solution. Using a spectrometer of Gemini-200 (200 MHz; Varian), Gemini-300 (300 MHz; Varian), Mercury 400 (400 MHz; Varian) or Inova 400 (400 MHz; Varian), each sample was analyzed for the total δ value in ppm.

The meanings of the abbreviations in the following Examples are mentioned below.
i-Bu: isobutyl group
n-Bu: n-butyl group
t-Bu: t-butyl group
Me: methyl group
Et: ethyl group
Ph: phenyl group
i-Pr: isopropyl group
n-Pr: n-propyl group
CDCl$_3$: heavy chloroform
CD$_3$OD: heavy methanol
DMSO-d$_6$: heavy dimethylsulfoxide
The meanings of the abbreviations in nuclear magnetic resonance spectra are mentioned below.

s: singlet
d: doublet
dd: double-doublet
t: triplet
m: multiplet
br: broad
q: quartet
J: coupling constant
Hz: hertz Example 1

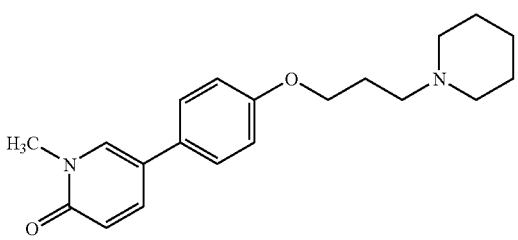

1-Methyl-5-{4-[3-(1-piperidinyl)propoxy]phenyl}-2(1H)-pyridone

1) Production of 4-(3-chloropropoxy)iodobenzene

1-Bromo-3-chloropropane (21.4 g, 136 mmol) and potassium carbonate (30 g, 217 mmol) were added to an acetone (300 mL) solution of 4-iodophenol (20 g, 90.9 mmol), and stirred under reflux for 20 hours. The reaction mixture was cooled to room temperature, filtered, and the filtrate was concentrated under reduced pressure to obtain the entitled compound (30 g, 100%).

1) Production of 4,4,5,5-tetramethyl-2-(4-(3-chloropropoxy)phenyl)-1,3,2-dioxaborolane Potassium acetate (1.18 g, 12.0 mmol) and bis(diphenylphosphino)ferrocene palladium(II)dichloride-dichloromethane (176 mg, 0.24 mmol) were added to a dimethylsulfoxide (70 mL) solution of the compound (1.3 g, 4.38 mmol) obtained in the above reaction and bis(pinacolato)diboron (1.32 g, 5.21 mmol), and stirred in a nitrogen atmosphere at 80° C. for 0.5 hours. The reaction mixture was cooled to room temperature, water was added to it, and extracted with ethyl acetate. The organic layer was washed with saturated brine, dried with anhydrous magnesium sulfate, and concentrated under reduced pressure. The residue was purified through silica gel column chromatography (C-300, hexane/ethyl acetate=8/1) to obtain the entitled compound (482 mg, 41%).

2) Production of 5-{4-(3-chloropropoxy)phenyl}-1-methyl-2(1H)-pyridone

Aqueous 2 N sodium hydroxide solution (0.2 mL) and tetrakis(triphenylphosphine)palladium(0) (15 mg, 0.013 mmol) were added to a dimethoxyethane (3 mL) solution of the compound (87 mg, 0.29 mmol) obtained in the above reaction and 5-bromo-1-methyl-2(1H)-pyridone (50 mg, 0.27 mmol), and stirred in a nitrogen atmosphere at 90° C. for 23 hours. The reaction mixture was cooled to room temperature, and extracted with ethyl acetate. The organic layer was washed with saturated brine, dried with anhydrous magnesium sulfate, and concentrated under reduced pressure. The residue was purified through silica gel column chromatography (C-300, ethyl acetate/hexane=1/1) to obtain the entitled compound (43 mg, 58%).

3) Potassium iodide (50 mg, 0.30 mmol) and potassium carbonate (42 mg, 0.30 mmol) were added to a dimethylformamide (3 mL) solution of the compound (42 mg, 0.15 mmol) obtained in the above reaction and piperidine (0.02 mL, 0.20 mmol), and stirred in a nitrogen atmosphere at 80° C. for 16 hours. The reaction mixture was cooled to room temperature, and extracted with chloroform. The organic layer was washed with saturated brine, dried with anhydrous magnesium sulfate and concentrated under reduced pressure. The residue was purified through amine-type silica gel column chromatography (Biotage NH, ethyl acetate/hexane=1/1) to obtain the entitled compound (28 mg, 57%).

$^1$HNMR (300 MHz, CDCl$_3$, δ ppm): 1.42-1.47 (2H, m), 1.60-1.63 (4H, m), 1.94-2.03 (2H, m), 2.40-2.50 (6H, m), 3.61 (3H, s), 4.03 (2H, t, J=6.4 Hz), 6.64 (1H, d, J=9.3 Hz), 6.94 (2H, d, J=8.7 Hz), 7.30 (2H, d, J=8.7 Hz), 7.41 (1H, d, J=2.3 Hz), 7.57 (1H, dd, J=2.6, 9.3 Hz);

Mass Spectrum (ESI): 327 (M+H).

Example 2

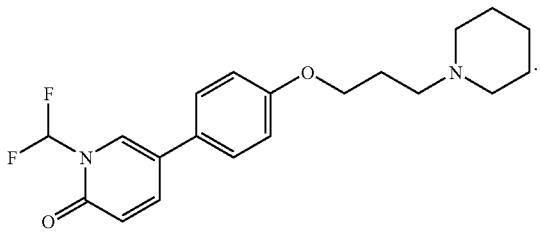

1-Difluoromethyl-5-{4-[3-(1-piperidinyl)propoxy]phenyl}-2(1H)-pyridone

Using the intermediate obtained in Example 1-1) and 5-bromo-1-difluoromethyl-2(1H)-pyridone, the entitled compound was obtained in the same manner as in Example 1-2) and 1-3).

$^1$HNMR (300 MHz, CDCl$_3$, δ ppm): 1.42-1.48 (2H, m), 1.56-1.65 (4H, m), 1.94-2.01 (2H, m), 2.39-2.50 (6H, m), 4.04 (2H, t, J=6.4 Hz), 6.63 (1H, d, J=9.6 Hz), 6.96 (2H, d, J=8.6 Hz), 7.33 (2H, d, J=8.8 Hz), 7.54-7.55 (1H, m), 7.64 (1H, dd, J=2.5, 9.6 Hz), 7.75 (1H, t, J=60.4 Hz);

Mass Spectrum (ESI): 363 (M+H).

Example 3

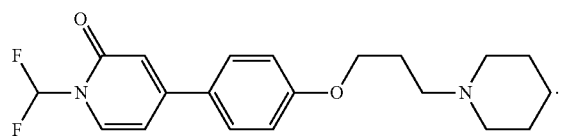

1-Difluoromethyl-4-{4-[3-(1-piperidinyl)propoxy]
phenyl}-2(1H)-pyridone

Using the intermediate obtained in Example 1-1) and 4-bromo-1-difluoromethyl-2(1H)-pyridone, the entitled compound was obtained in the same manner as in Example 1-2) and 1-3).

¹HNMR (300 MHz, CDCl₃, δ ppm): 1.43-1.49 (2H, m), 1.57-1.64 (4H, m), 1.98-2.03 (2H, m), 2.42-2.52 (6H, m), 4.047 (2H, t, J=6.4 Hz), 6.57 (1H, dd, J=1.8, 7.6 Hz), 6.70 (1H, d, J=0.9 Hz), 6.99 (2H, d, J=8.7 Hz), 7.48 (1H, d, J=7.5 Hz), 7.52-7.55 (2H, m), 7.72 (1H, t, J=60.6 Hz);
Mass Spectrum (ESI): 363 (M+H).

Example 4

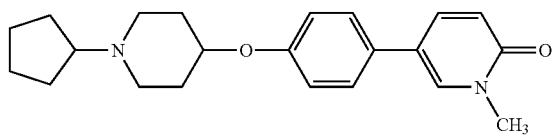

5-[4-(1-Cyclopentylpiperidin-4-yloxy)phenyl]-1-
methyl-2(1H)-pyridone

1) Production of
4-(4-iodophenoxy)-1-t-butoxycarbonylpiperidine

Potassium carbonate (15 g, 109 mmol) was added to a dimethylformamide (200 mL) solution of 4-iodophenol (8.0 g, 36.4 mmol) and 1-t-butoxycarbonyl-4-methanesulfonyloxypiperidine (13.2 g, 47.3 mmol), and stirred at 80° C. for 24 hours. The reaction mixture was cooled to room temperature, then aqueous 2 N sodium hydroxide solution was added to the reaction mixture, and extracted with diethyl ether. The organic layer was washed with saturated brine, dried with anhydrous sodium sulfate, and concentrated under reduced pressure. The residue was purified through silica gel column chromatography (C-300, hexane/ethyl acetate=4/1) to obtain the entitled compound (12 g, 82

2) Production of 4-(4,4,5,5-tetramethyl-1,3,2-dioxoborolan-2-yl)phenoxy-1-t-butoxycarbonylpiperidine Potassium acetate (2.92 g, 29.8 mmol) and bis(diphenylphosphino)ferrocene palladium(II)dichloride-dichloromethane (486 mg, 0.60 mmol) were added to a dimethylsulfoxide (35 mL) solution of the compound (4.0 g, 9.92 mmol) obtained in the above reaction and bis(pinacolato)diboron (3.27 g, 12.9 mmol), and stirred in a nitrogen atmosphere at 75° C. for 2 hours. The reaction mixture was cooled to room temperature, water was added to it, and extracted with ethyl acetate. The organic layer was washed with saturated brine, dried with anhydrous magnesium sulfate, and concentrated under reduced pressure. The residue was purified through silica gel column chromatography (C-300, hexane/ethyl acetate=8/1) to obtain the entitled compound (2.14 g, 57%) as a pale yellow solid.

3) Production of 5-[4-(1-t-butoxycarbonylpiperidin-
4-yloxy)phenyl]-1-methyl-2(1H)-pyridone Aqueous 2 N sodium carbonate solution (0.2 mL) and tetrakis(triphenylphosphine)palladium(0) (15 mg, 0.013 mmol) were added to a dimethoxyethane (2 mL) solution of the compound (118 mg, 0.29 mmol) obtained in the above reaction and 5-bromo-1-methyl-2(1H)-pyridone (50 mg, 0.27 mmol), and stirred in a nitrogen atmosphere at 90° C. for 4 hours. The reaction mixture was cooled to room temperature, water was added to it, and extracted with ethyl acetate. The organic layer was washed with saturated brine, dried with anhydrous magnesium sulfate, and concentrated under reduced pressure. The residue was purified through silica gel column chromatography (C-300, ethyl acetate/hexane=2/1) to obtain the entitled compound (102 mg, 100%).

3) Production of 5-[4-(piperidin-4-yloxy)phenyl]-1-
methyl-2(1H)-pyridone

With cooling with ice, trifluoroacetic acid (0.3 mL) was added to a chloroform (2 mL) solution of the compound (102 mg, 0.27 mmol) obtained in the above reaction, and stirred at that temperature for 2.5 hours. The reaction mixture was made basic with saturated sodium bicarbonate water, and extracted three times with chloroform. The organic layer was dried with anhydrous magnesium sulfate and concentrated under reduced pressure to obtain a crude oil of the entitled compound.

4) Sodium cyanotrihydroborate (25 mg, 0.41 mmol) and zinc chloride (7.0 mg, 0.054 mmol) were added to a methanol (3 mL) solution of the compound obtained in the above reaction and cyclopentanone (0.036 mL, 0.41 mmol), and stirred at room temperature for 1 hour. Water was added to the reaction mixture, and extracted twice with chloroform. The organic layer was washed with saturated brine, dried with anhydrous magnesium sulfate, and concentrated under reduced pressure. The residue was purified through amine-type silica gel chromatography (Biotage NH, ethyl acetate/hexane=2/1) to obtain the entitled compound (73 mg, 77%) as a pale yellow solid.

¹HNMR (300 MHz, CDCl₃, δ ppm): 1.38-1.70 (6H, m), 1.83-1.90 (4H, m), 1.99-2.05 (2H, m), 2.30-2.37 (2H, m), 2.50-2.55 (1H, m), 2.78-2.81 (2H, m), 3.61 (3H, s), 4.32-4.35 (1H, m), 6.64 (1H, d, J=9.3 Hz), 6.94 (2H, d, J=8.6 Hz), 7.29 (2H, d, J=8.7 Hz), 7.41 (1H, d, J=2.6 Hz), 7.57 (1H, dd, J=2.6, 9.3 Hz);
Mass Spectrum (ESI): 353 (M+H).

Example 5

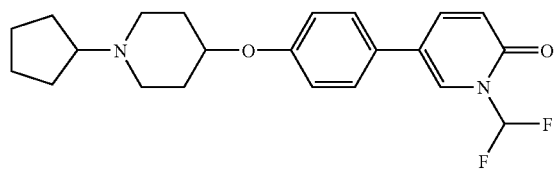

5-[4-(1-Cyclopentylpiperidin-4-yloxy)phenyl]-1-
difluoromethyl-2(1H)-pyridone

Using the intermediate obtained in Example 4-1) and 5-bromo-1-difluoromethyl-2(1H)-pyridone, the entitled compound was obtained in the same manner as in Example 4-2), 4-3) and 44).

¹HNMR (300 MHz, CDCl₃, δ ppm): 1.39-1.73 (6H, m), 1.84-1.91 (4H, m), 2.00-2.06 (2H, m), 2.32-2.38 (2H, m), 2.51-2.56 (1H, m), 2.78-2.82 (2H, m), 4.34-4.38 (1H, m), 6.64 (1H, d, J=9.6 Hz), 6.97 (2H, d, J=8.6 Hz), 7.33 (2H, d, J=8.6 Hz), 7.54-7.55 (1H, m), 7.64 (1H, dd, J=2.3, 9.7 Hz), 7.75 (1H, t, J=60.3 Hz);

Mass Spectrum (ESI): 389 (M+H).

Example 6

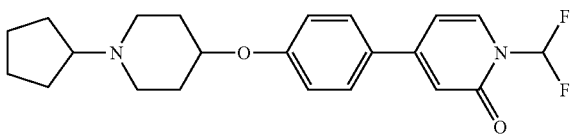

4-[4-(1-Cyclopentylpiperidin-4-yloxy)phenyl]-1-difluoromethyl-2(1H)-pyridone

Using the intermediate obtained in Example 4-1) and 4-iodo-1-difluoromethyl-2(1H)-pyridone, the entitled compound was obtained in the same manner as in Example 4-2), 4-3) and 44).

¹HNMR (300 MHz, CDCl₃, δ ppm): 1.39-1.73 (6H, m), 1.84-1.91 (4H, m), 2.00-2.07 (2H, m), 2.33-2.40 (2H, m), 2.51-2.56 (1H, m), 2.78-2.83 (2H, m), 4.37-4.41 (1H, m), 6.57 (1H, dd, J=1.7, 7.6 Hz), 6.70 (1H, brs), 6.99 (2H, d, J=8.7 Hz), 7.48 (1H, d, J=7.6 Hz), 7.53 (2H, d, J=8.6 Hz), 7.72 (1H, t, J=60.6 Hz);

Mass Spectrum (ESI): 389 (M+H).

Example 7

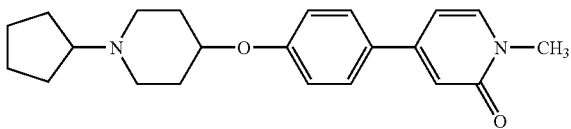

4-[4-(1-Cyclopentylpiperidin-4-yloxy)phenyl]-1-methyl-2(1H)-pyridone

Using the intermediate obtained in Example 4-1) and 4-iodo-1-methyl-2(1H)-pyridone, the entitled compound was obtained in the same manner as in Example 4-2), 4-3) and 4-4).

¹HNMR (300 MHz, CDCl₃, δ ppm): 1.38-1.72 (6H, m), 1.83-1.90 (4H, m), 2.00-2.06 (2H, m), 2.31-2.38 (2H, m), 2.50-2.55 (1H, m), 2.77-2.81 (2H, m), 3.56 (3H, s), 4.36-4.40 (1H, m), 6.41 (1H, dd, J=2.0, 7.2 Hz), 6.75 (1H, d, J=1.9 Hz), 6.96 (2H, d, J=8.6 Hz), 7.29 (1H, d, J=7.0 Hz), 7.51 (2H, d, J=8.6 Hz);

Mass Spectrum (ESI): 353 (M+H).

Example 8

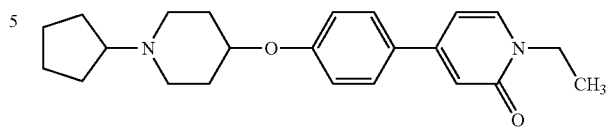

4-[4-(1-Cyclopentylpiperidin-4-yloxy)phenyl]-1-ethyl-2(1H)-pyridone

Using the intermediate obtained in Example 4-1) and 4-iodo-1-ethyl-2(1H)-pyridone, the entitled compound was obtained in the same manner as in Example 4-2), 4-3) and 4-4).

¹HNMR (300 MHz, CDCl₃, δ ppm): 1.40-1.73 (9H, m), 1.87-1.94 (4H, m), 2.04-2.10 (2H, m), 2.35-2.42 (2H, m), 2.54-2.59 (1H, m), 2.82-2.85 (2H, m), 4.05 (2H, q, J=7.2 Hz), 4.40-4.42 (1H, m), 6.46 (1H, dd, J=2.0, 7.1 Hz), 6.78 (1H, d, J=1.9 Hz), 7.00 (2H, d, J=8.8 Hz), 7.33 (1H, d, J=7.1 Hz), 7.55 (2H, d, J=8.8 Hz);

Mass Spectrum (ESI): 367 (M+H).

Example 9

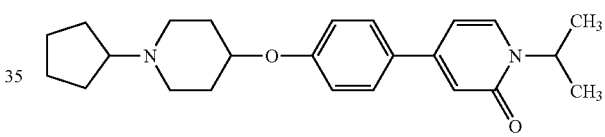

4-[4-(1-Cyclopentlpipieridin-4-yloxy)phenyl]-1-(1-methylethyl)-2(1H)-pyridone

Using the intermediate obtained in Example 4-1) and 4-iodo-1-isopropyl-2(1H)-pyridone, the entitled compound was obtained in the same manner as in Example 4-2), 4-3) and 44).

¹HNMR (300 MHz, CDCl₃, δ ppm): 1.37-1.73 (12H, m), 1.82-1.90 (4H, m), 1.99-2.07 (2H, m), 2.32-2.38 (2H, m), 2.50-2.56 (1H, m), 2.78-2.84 (2H, m), 4.35-4.40 (1H, m), 5.26-5.35 (1H, m), 6.46 (1H, dd, J=2.0, 7.3 Hz), 6.74 (1H, d, J=2.0 Hz), 6.96 (2H, d, J=8.8 Hz), 7.35 (1H, d, J=7.3 Hz), 7.51 (2H, d, J=8.6 Hz);

Mass Spectrum (ESI): 381 (M+H).

Example 10

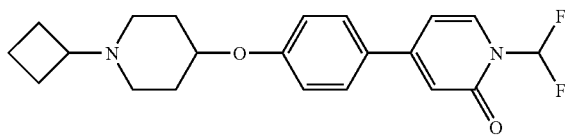

4-[4-(1-Cyclobutylpiperidin-4-yloxy)phenyl]-1-difluoromethyl-2(1H)-pyridone

1) Production of 4-[4-(piperidin-4-yloxy)phenyl]-1,1-difluoromethyl-2(H1H)-pyridone Using the intermediate obtained in Example 4-1) and 4-iodo-1-difluoromethyl-2(1H)-pyridone, the entitled compound was obtained in the same manner as in Example 4-2) and 4-3).

2) With cooling with ice, sodium cyanotrihydroborate (41 mg, 0.65 mmol) and zinc chloride (14 mg, 0.1 mmol) were added to a methanol (5 mL) solution of the compound (160 mg, 0.5 mmol) obtained in the above reaction and cyclobutanone (0.049 mL, 0.65 mmol), and stirred at room temperature for 1.5 hours. Water was added to the reaction mixture, and extracted twice with chloroform. The organic layer was washed with saturated brine, dried with anhydrous magnesium sulfate and concentrated under reduced pressure. The residue was purified through amine-type silica gel chromatography (Biotage NH, ethyl acetate/hexane=1/6) to obtain the entitled compound (86 mg, 46%) as a pale yellow solid.

$^1$HNMR (300 MHz, CDCl$_3$, δ ppm): 1.68-1.92 (6H, m), 1.98-2.06 (4H, m), 2.14-2.20 (2H, m), 2.59-2.65 (2H, m), 2.72-2.77 (1H, m), 4.38-4.41 (1H, m), 6.56 (1H, dd, J=1.3, 7.7 Hz), 6.70 (1H, brs), 6.98 (2H, d, J=8.8 Hz), 7.47 (1H, d, J=7.6 Hz), 7.53 (2H, d, J=8.6 Hz), 7.72 (1H, t, J=60.3 Hz);

Mass Spectrum (ESI): 375 (M+H).

Example 11

5-[4-(1-Cyclopentylpiperidin-4-yloxy)phenyl]-1-methoxy-2(1H)-pyridone

Using the intermediate obtained in Example 4-1) and 4-bromo-1-methoxy-2(1H)-pyridone, the entitled compound was obtained in the same manner as in Example 4-2), 4-3) and 44).

$^1$HNMR (300 MHz, CDCl$_3$, δ ppm): 1.41-1.75 (6H, m), 1.86-1.94 (4H, m), 2.00-2.08 (2H, m), 2.33-2.40 (2H, m), 2.52-2.58 (1H, m), 2.79-2.88 (2H, m), 4.15 (3H, s), 4.35-4.39 (1H, m), 6.77 (1H, d, J=9.5 Hz), 6.98 (2H, d, J=8.7 Hz), 7.33 (2H, d, J=8.7 Hz), 7.59 (1H, dd, J=2.6, 9.5 Hz), 7.69 (1H, d, J=2.6 Hz);

Mass Spectrum (ESI): 369 (M+H).

Example 12

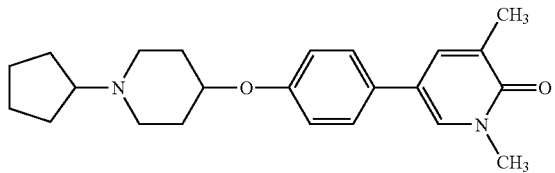

5-[4-(1-Cyclopentylpiperidin-4-yloxy)phenyl]-1,3-dimethyl-2(1H)-pyridone

Using the intermediate obtained in Example 4-1) and 4-bromo-1,4-dimethyl-2(1H)-pyridone, the entitled compound was obtained in the same manner as in Example 4-2), 4-3) and 4-4).

$^1$HNMR (300 MHz, CDCl$_3$, δ ppm): 1.38-1.68 (6H, m), 1.83-1.89 (4H, m), 2.00-2.05 (2H, m), 2.21 (3H, s), 2.31-2.37 (2H, m), 2.50-2.55 (1H, m), 2.78-2.83 (2H, m), 3.61 (3H, s), 4.32-4.34 (1H, m), 6.93 (2H, d, J=8.6 Hz), 7.25-7.31 (3H, m), 7.45 (1H, d, J=1.1 Hz);

Mass Spectrum (ESI): 367 (M+H).

Example 13

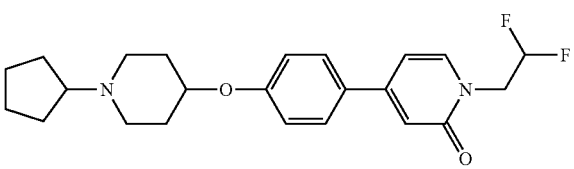

4-[4-(1-Cyclonentylpiperidin-4-yloxy)phenyl]-1-(2,2-difluoroethyl)-2(1H)-pyridone Using the intermediate obtained in Example 4-1) and 4-iodo-1-(2,2-difluoroethyl)-2(1H)-pyridone, the entitled compound was obtained in the same manner as in Example 4-2), 4-3) and 44).

$^1$HNMR (300 MHz, CDCl$_3$, δ ppm): 1.36-1.76 (6H, m), 1.81-1.89 (4H, m), 1.99-2.07 (2H, m), 2.32-2.41 (2H, m), 2.50-2.56 (1H, m), 2.78-2.87 (2H, m), 4.26 (2H, dt, J=4.7, 13.8 Hz), 4.35-4.41 (1H, m), 5.95-6.36 (1H, m), 6.47 (1H, dd, J=1.0, 6.1 Hz), 6.75 (1H, brs), 6.99 (2H, d, J=8.1 Hz), 7.26-7.29 (1H, m), 7.52 (2H, d, J=8.0 Hz);

Mass Spectrum (ESI): 403 (M+H).

Example 14

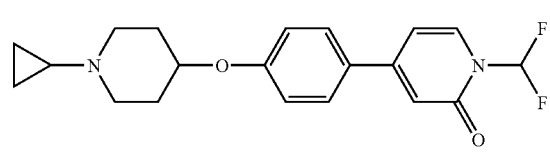

4-[4-(1-Cyclopropylpiperidin-4-yloxy)phenyl]-1-difluoromethyl-2(1H)-pyridone Sodium cyanotrihydroborate (56 mg, 0.69 mmol) was added to a methanol (5 mL) solution of the compound (189 mg, 0.59 mmol) obtained in Example 10-1), 1-methoxy-1-trimethylsiloxycyclopropane (0.24 mL, 1.18 mmol), acetic acid (0.24 mL, 1.18 mmol) and 3 Å molecular sieve (200 mg), and stirred at 65° C. for 7 hours. Water was added to the reaction mixture, and extracted twice with chloroform. The organic layer was washed with saturated brine, dried with anhydrous magnesium sulfate and concentrated under reduced pressure. The residue was purified through amine-type silica gel chromatography (Biotage NH, ethyl acetate/hexane=1/7) to obtain the entitled compound (98 mg, 46%) as a colorless solid.

$^1$HNMR (300 MHz, CDCl$_3$, δ ppm): 0.43-0.49 (4H, m), 1.62-1.67 (1H, m), 1.79-1.85 (2H, m), 1.97-2.03 (2H, m), 2.48-2.54 (2H, m), 2.88-2.93 (2H, m), 4.40-4.42 (1H, m), 6.57 (1H, dd, J=1.9, 7.5 Hz), 6.71 (1H, brs), 7.00 (2H, d, J=8.8 Hz), 7.49 (1H, d, J=7.5 Hz), 7.54 (2H, d, J=8.8 Hz), 7.73 (1H, t, J=60.4 Hz);
Mass Spectrum (ESI): 361 (M+H).

Example 15

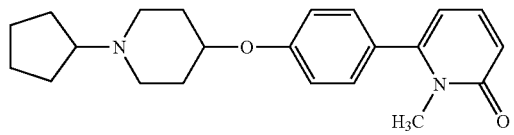

6-[4-(1-Cyclopentylpiperidin-4-yloxy)phenyl]-1-methyl-2(1H)-pyridone

Using the intermediate obtained in Example 4-1) and 6-bromo-1-methyl-2(1H)-pyridone, the entitled compound was obtained in the same manner as in Example 4-2), 4-3) and 4-4).

$^1$HNMR (300 MHz, CDCl$_3$, δ ppm): 1.39-1.73 (6H, m), 1.83-1.93 (4H, m), 2.01-2.08 (2H, m), 2.31-2.39 (2H, m), 2.51-2.56 (1H, m), 2.79-2.85 (2H, m), 3.39 (3H, s), 4.36-4.39 (1H, m), 6.07 (1H, dd, J=1.3, 6.9 Hz), 6.57 (1H, dd, J=1.3, 9.1 Hz), 6.97 (2H, d, J=8.7 Hz), 7.24 (2H, d, J=8.7 Hz), 7.32 (1H, dd, J=6.9, 9.1 Hz);
Mass Spectrum (ESI): 353 (M+H).

Example 16

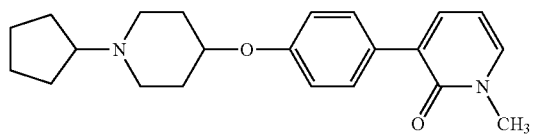

3-[4-(1-Cyclopentylpiperidin-4-yloxy)phenyl]-1-methyl-2(1H)-pyridone

Using the intermediate obtained in Example 4-1) and 3-bromo-1-methyl-2(1H)-pyridone, the entitled compound was obtained in the same manner as in Example 4-2), 4-3) and 44).

$^1$HNMR (300 MHz, CDCl$_3$, δ ppm): 1.38-1.72 (6H, m), 1.84-1.90 (4H, m), 1.98-2.06 (2H, m), 2.31-2.37 (2H, m), 2.50-2.55 (1H, m), 2.77-2.83 (2H, m), 3.61 (3H, s), 4.34-4.37 (1H, m), 6.20-6.91 (1H, m), 6.93 (2H, d, J=8.3 Hz), 7.25-7.28 (1H, m), 7.42 (1H, dd, J=1.4, 7.0 Hz), 7.64 (2H, d, J=8.4 Hz);
Mass Spectrum (ESI): 353 (M+H).

Example 17

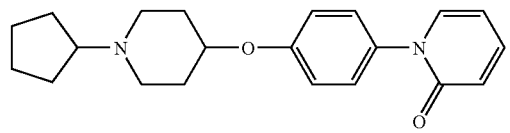

1-[4-(1-Cyclopentylpiperidin-4-yloxy)phenyl]-2(1H)-pyridone

1) Production of 1-{4-methoxyphenyl}-2(1H)-pyridone

Potassium carbonate (1.16 g, 8.41 mmol) and copper iodide (16 mg, 0.084 mmol) were added to a dimethylformamide (12 mL) solution of 4-hydroxypyridine (800 mg, 8.41 mmol) and 4-iodo-1-methoxybenzene (3.94 g, 16.8 mmol), and stirred at 150° C. for 21 hours. The reaction mixture was cooled to room temperature, then water was added to the reaction mixture, and extracted with ethyl acetate. The organic layer was washed with saturated brine, dried with anhydrous sodium sulfate, and then concentrated under reduced pressure. The residue was purified through silica gel column chromatography (C-300, hexane/ethyl acetate=1/1) to obtain the entitled compound (870 mg, 51%).

2) Production of 1-{4-hydroxyphenyl}-2(1H)-pyridone

At 50° C., boron trifluoride (1.43 mL, 2.0 mmol) was added to a chloroform (3 mL) solution of the compound (201 mg, 1.0 mmol) obtained in the above reaction, and stirred in a nitrogen atmosphere at 75° C. for 8 hours. The reaction mixture was cooled to room temperature, then water was added to it, and extracted with chloroform. The organic layer was washed with saturated brine, dried with anhydrous magnesium sulfate, and then concentrated under reduced pressure. The residue was crystallized from diethyl ether/hexane mixture to obtain the entitled compound (80 mg, 43%) as a pale yellow solid.

3) Production of 1-[4-(1-t-butoxycarbonylpiperidin-4-yloxy)phenyl]-2(1H)-pyridone Cesium carbonate (272 mg, 0.83 mmol) was added to a dimethylformamide (3 mL) solution of the compound (78 mg, 0.42 mmol) obtained in the above reaction and 4-methanesulfonyloxy-1-t-butoxycarbonylpiperidine (140 mg, 0.50 mmol), and stirred at 90° C. for 4 hours. The reaction mixture was cooled to room temperature, water was added to the reaction mixture, and extracted with ethyl acetate. The organic layer was washed with saturated brine, dried with anhydrous sodium sulfate, and then concentrated under reduced pressure. The residue was purified through silica gel column chromatography (C-300, hexane/ethyl acetate=2/3) to obtain the entitled compound (132 mg, 86%) as a colorless solid.

4) Production of 5-[4-(piperidin-4-yloxy)phenyl]-1-methyl-2(1H)-pyridone

With cooling with ice, trifluoroacetic acid (0.4 mL) was added to a chloroform (2 mL) solution of the compound (131 mg, 0.33 mmol) obtained in the above reaction, and stirred at that temperature for 1.5 hours. The reaction mixture was made basic with saturated sodium bicarbonate water, and extracted four times with chloroform. The organic layer was dried with anhydrous magnesium sulfate, and concentrated under reduced pressure to obtain a crude oil of the entitled compound.
4) Sodium cyanotrihydroborate (29 mg, 0.46 mmol) and zinc chloride (10.0 mg, 0.074 mmol) were added to a methanol (4 mL) solution of the compound obtained in the above reaction and cyclopentanone (0.040 mL, 0.46 mmol), and stirred at room temperature for 1.5 hours. Water was added to the reaction mixture, and extracted twice with chloroform. The organic layer was washed with saturated brine, dried with anhydrous magnesium sulfate, and concentrated under reduced pressure to obtain the entitled compound (102 mg, 72%) as a colorless solid.

$^1$HNMR (300 MHz, DMSO-d$_6$, δ ppm): 1.39-1.73 (6H, m), 1.84-1.89 (4H, m), 2.00-2.05 (2H, m), 2.32-2.39 (2H, m), 2.50-2.55 (1H, m), 2.77-2.80 (2H, m), 4.34-4.38 (1H, m), 6.21 (1H, dd, J=1.3, 6.6 Hz), 6.65 (1H, d, J=9.2 Hz), 6.98 (2H, d, J=8.9 Hz), 7.25-7.41 (4H, m);
Mass Spectrum (ESI): 339 (M+H).

Example 18

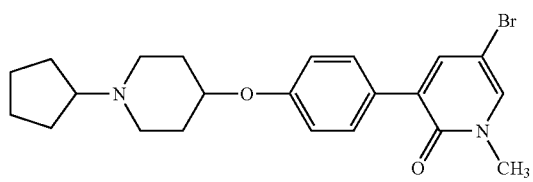

5-Bromo-3-[4-(1-cyclopentylpiperidin-4-yloxy)phenyl]-1-methyl-2(1H)-pyridone

Using the intermediate obtained in Example 4-1) and 5-bromo-3-chloro-1-methyl-2(1H)-pyridone, the entitled compound was obtained in the same manner as in Example 4-2), 4-3) and 4-4).

$^1$HNMR (300 MHz, CDCl$_3$, δ ppm): 1.38-1.72 (6H, m), 1.83-1.92 (4H, m), 1.99-2.06 (2H, m), 2.31-2.38 (2H, m), 2.50-2.55 (1H, m), 2.76-2.80 (2H, m), 3.58 (3H, s), 4.35-4.37 (1H, m), 6.93 (2H, d, J=8.8 Hz), 7.39 (1H, d, J=2.7 Hz), 7.49 (1H, d, J=2.7 Hz), 7.62 (2H, d, J=8.8 Hz);
Mass Spectrum (ESI): 431,433 (M+H).

Example 19

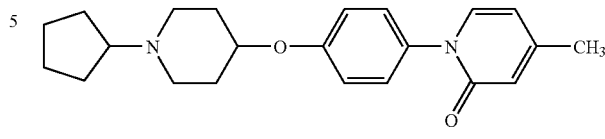

1-[4-(1-Cyclopentylpiperidin-4-yloxy)phenyl]-4-methyl-2(1H)-pyridone

The entitled compound was obtained in the same manner as in Example 17, in which, however, 4-methyl-2-hydroxypyridine was used.

$^1$HNMR (300 MHz, CDCl$_3$, δ ppm): 1.39-1.75 (6H, m), 1.84-1.92 (4H, m), 1.99-2.07 (2H, m), 2.23 (3H, s), 2.31-2.38 (2H, m), 2.50-2.56 (1H, m), 2.77-2.80 (2H, m), 4.33-4.37 (1H, m), 6.06 (1H, dd, J=1.8, 7.0 Hz), 6.45 (1H, brs), 6.97 (2H, d, J=8.8 Hz), 7.20-7.28 (3H, m);
Mass Spectrum (ESI): 353 (M+H).

Example 20

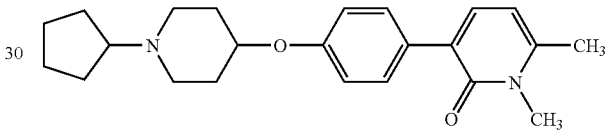

3-[4-(1-Cyclopentylpiperidin-4-yloxy)phenyl]-1,6-dimethyl-2(1H)-pyridone

Using the intermediate obtained in Example 4-1) and 3-bromo-1,6-dimethyl-2(1H)-pyridone, the entitled compound was obtained in the same manner as in Example 4-2), 4-3) and 4-4).

$^1$HNMR (300 MHz, CDCl$_3$, δ ppm): 1.38-1.72 (6H, m), 1.83-1.90 (4H, m), 1.97-2.05 (2H, m), 2.30-2.38 (5H, m), 2.49-2.55 (1H, m), 2.76-2.82 (2H, m), 3.59 (3H, s), 4.33-4.36 (1H, m), 6.11 (1H, d, J=7.2 Hz), 6.92 (2H, d, J=8.8 Hz), 7.34 (1H, d, J=7.2 Hz), 7.61 (2H, d, J=8.8 Hz);
Mass Spectrum (ESI): 367 (M+H).

Example 21

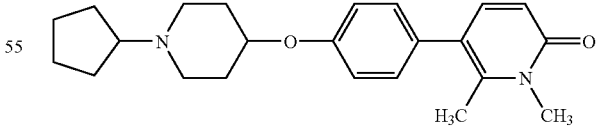

5-[4-(1-Cyclopentylpiperidin-4-yloxy)phenyl]-1,6-dimethyl-2(1H)-pyridone

Using the intermediate obtained in Example 4-1) and 5-bromo-1,6-dimethyl-2(1H)-pyridone, the entitled compound was obtained in the same manner as in Example 4-2), 4-3) and 44).

¹HNMR (300 MHz, CDCl₃, δ ppm): 1.40-1.73 (6H, m), 1.84-1.92 (4H, m), 2.02-2.08 (2H, m), 2.31-2.38 (5H, m), 2.51-2.56 (1H, m), 2.81-2.88 (2H, m), 3.62 (3H, s), 4.34-4.36 (1H, m), 6.52 (1H, d, J=9.2 Hz), 6.94 (2H, d, J=8.6 Hz), 7.11 (2H, d, J=8.6 Hz), 7.14-7.27 (1H, m);

Mass Spectrum (ESI): 367 (M+H).

Example 22

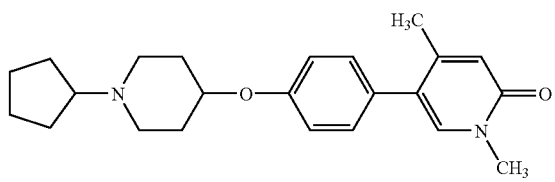

5-[4-(1-Cyclopentylpiperidin-4-yloxy)phenyl]-1,4-dimethyl-2(1H)-pyridone

Using the intermediate obtained in Example 4-1) and 5-bromo-1,4-dimethyl-2(1H)-pyridone, the entitled compound was obtained in the same manner as in Example 4-2), 4-3) and 44).

¹HNMR (300 MHz, CDCl₃, δ ppm): 1.39-1.73 (6H, m), 1.82-1.90 (4H, m), 2.01-2.08 (5H, m), 2.32-2.38 (2H, m), 2.51-2.56 (1H, m), 2.81-2.83 (2H, m), 3.54 (3H, s), 4.33-4.36 (1H, m), 6.47 (1H, s), 6.92 (2H, d, J=8.6 Hz), 7.10-7.15 (3H, m);

Mass Spectrum (ESI): 367 (M+H).

Example 23

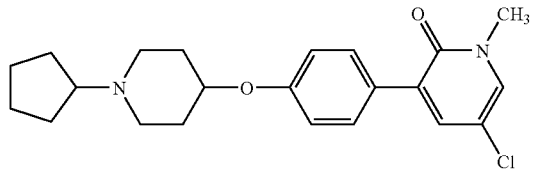

5-Chloro-3-[4-(1-cyclopentylpiperidin-4-yloxy)phenyl]-1-methyl-2(1H)-pyridone

Using the intermediate obtained in Example 4-1) and 3-bromo-5-chloro-1-methyl-2(1H)-pyridone, the entitled compound was obtained in the same manner as in Example 4-2), 4-3) and 44).

¹HNMR (300 MHz, CDCl₃, δ ppm): 1.40-1.72 (6H, m), 1.82-1.91 (4H, m), 1.99-2.05 (2H, m), 2.32-2.38 (2H, m), 2.49-2.55 (1H, m), 2.78-2.80 (2H, m), 3.58 (3H, s), 4.35-4.39 (1H, m), 6.93 (2H, d, J=8.6 Hz), 7.30 (1H, d, J=2.9 Hz), 7.41 (1H, d, J=2.9 Hz), 7.63 (2H, d, J=8.6 Hz);

Mass Spectrum (ESI): 387 (M+H).

Example 24

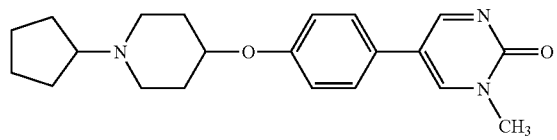

5-[4-(1-Cyclopentylpiperidin-4-yloxy)phenyl]-1-methyl-2(1H)-pyrimidone

1) Production of 5-bromo-1-methyl-2(1H)-pyrimidone

With cooling with ice, potassium carbonate (7.56 g, 54.7 mmol) and methyl iodide (1.27 ml, 20.3 mmol) were added to a dimethyl sulfoxide (100 mL) solution of 5-bromo-2-hydroxypyrimidine hydrobromide (4.0 g, 15.6 mmol), and stirred at 15° C. for 16 hours. Water was added to the reaction mixture, and extracted three times with ethyl acetate. The organic layer was washed with saturated brine, dried with anhydrous sodium sulfate and then concentrated under reduced pressure. The residue was suspended in ethyl acetate, then filtered and dried to obtain the entitled compound (1.33 g, 45%).

2) Using 5-bromo-1-methyl-2(1H)-pyrimidine obtained in the above reaction and the intermediate obtained in Example 4-1), the entitled compound was obtained in the same manner as in Example 4-2), 4-3) and 44).

¹HNMR (300 MHz, CDCl₃, δ ppm): 1.40-1.74 (6H, m), 1.84-1.94 (4H, m), 2.00-2.08 (2H, m), 2.33-2.39 (2H, m), 2.51-2.57 (1H, m), 2.79-2.83 (2H, m), 3.66 (3H, s), 4.35-4.38 (1H, m), 6.99 (2H, d, J=8.7 Hz), 7.31 (2H, d, J=8.7 Hz), 7.76 (1H, d, J=3.3 Hz), 8.85 (1H, d, J=3.4 Hz);

Mass Spectrum (ESI): 354 (M+H).

Example 25

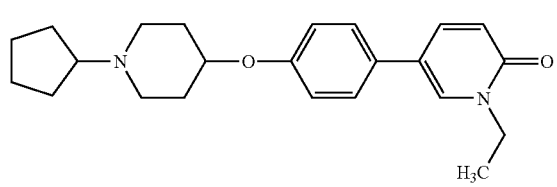

5-[4-(1-Cyclopentylpiperidin-4-yloxy)phenyl]-1-ethyl-2(1H)-pyridone

Using the intermediate obtained in Example 4-1) and 5-bromo-1-ethyl-2(1H)-pyridone, the entitled compound was obtained in the same manner as in Example 4-2), 4-3) and 44).

¹HNMR (300 MHz, CDCl₃, δ ppm): 1.38-1.72 (9H, m), 1.84-1.91 (4H, m), 2.00-2.06 (2H, m), 2.30-2.38 (2H, m), 2.50-2.56 (1H, m), 2.78-2.82 (2H, m), 4.02-4.09 (2H, m), 4.33-4.37 (1H, m), 6.64 (1H, d, J=9.5 Hz), 6.95 (2H, d, J=8.7 Hz), 7.31 (2H, d, J=8.7 Hz), 7.41 (1H, d, J=2.6 Hz), 7.56 (1H, dd, J=2.6, 9.4 Hz);

Mass Spectrum (ESI): 367 (M+H).

Example 26

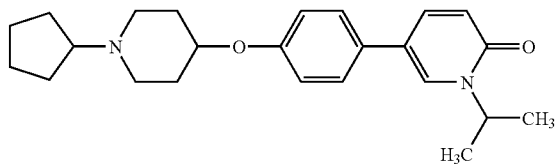

5-[4-(1-Cyclopentylpiperidin-4-yloxy)phenyl]-1-(1-methylethyl)-2(1H)-pyridone Using the intermediate obtained in Example 4-1) and 5-bromo-1-(1-methylmethyl)-2(1H)-pyridone, the entitled compound was obtained in the same manner as in Example 4-2), 4-3) and 4-4).

$^1$HNMR (300 MHz, CDCl$_3$, δ ppm): 1.36-1.73 (12H, m), 1.83-1.93 (4H, m), 2.00-2.06 (2H, m), 2.31-2.37 (2H, m), 2.50-2.55 (1H, m), 2.79-2.83 (2H, m), 4.33-4.36 (1H, m), 5.32-5.37 (1H, m), 6.63 (1H, d, J=9.4 Hz), 6.96 (2H, d, J=8.7 Hz), 7.31 (2H, d, J=8.7 Hz), 7.44 (1H, d, J=2.6 Hz), 7.53 (1H, dd, J=2.6, 9.3 Hz);

Mass Spectrum (ESI): 381 (M+H).

Example 27

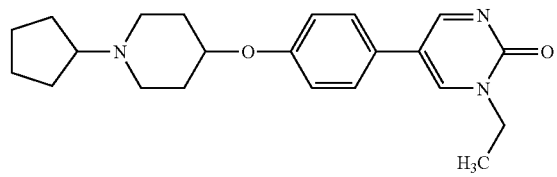

5-[4-(1-Cyclopentylpiperidin-4-yloxy)phenyl]-1-ethyl-2(1H)-primidone

1) Production of 5-bromo-1-ethyl-2(1H)pyrimidone

With cooling with ice, potassium carbonate (13.2 g, 95.7 mmol) and ethyl iodide (2.84 mL, 35.6 mmol) were added to a dimethyl sulfoxide (130 mL) solution of 5-bromo-2-hydroxypyrimidine hydrobromide (7.0 g, 27.3 mmol), and stirred at 15° C. for 16 hours. Water was added to the reaction mixture, and extracted three times with ethyl acetate. The organic layer was washed with saturated brine, dried with anhydrous sodium sulfate and then concentrated under reduced pressure. The organic layer was washed with saturated brine, dried with anhydrous sodium sulfate and concentrated under reduced pressure. The residue was purified through silica gel column chromatography (C-300, hexane/ethyl acetate=1/1) to obtain the entitled compound (3.34 g, 60%) as a colorless solid.

2) Using 5-bromo-1-ethyl-2(1H)-pyrimidone obtained in the above reaction and the intermediate obtained in Example 4-1, the entitled compound was obtained in the same manner as in Example 4-2), 4-3) and 4-4).

$^1$HNMR (300 MHz, CDCl$_3$, δ ppm): 1.38-1.73 (9H, m), 1.83-1.93 (4H, m), 2.00-2.06 (2H, m), 2.31-2.39 (2H, m), 2.50-2.56 (1H, m), 2.78-2.81 (2H, m), 4.04 (2H, q, J=7.2 Hz), 4.34-4.37 (1H, m), 6.98 (2H, d, J=8.8 Hz), 7.31 (2H, d, J=8.8 Hz), 7.73 (1H, d, J=3.4 Hz), 8.82 (1H, d, J=3.4 Hz);

Mass Spectrum (ESI): 368 (M+H).

Example 28

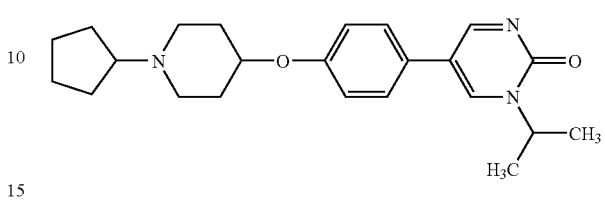

5-[4-(1-Cyclopentylpiperidin-4-yloxy)phenyl]-1-(1-methylethyl)-2(1H)-pyrimidone 1) Production of 5-bromo-1-(1-methylethyl)-2(1H)-pyrimidone With cooling with ice, potassium carbonate (17 g, 123 mmol) and isopropyl iodide (4.56 mL, 45.7 mmol) were added to a dimethyl sulfoxide (150 mL) solution of 5-bromo-2-hydroxypyrimidine hydrobromide (9.0 g, 35.2 mmol), and stirred at 15° C. for 16 hours. Water was added to the reaction mixture, and extracted three times with ethyl acetate. The organic layer was washed with saturated brine, dried with anhydrous sodium sulfate, and concentrated under reduced pressure. The organic layer was washed with saturated brine, dried with anhydrous sodium sulfate and concentrated under reduced pressure. The residue was purified through silica gel column chromatography (C-300, hexane/ethyl acetate=3/2) to obtain the entitled compound (2.34 g, 31%) as a colorless solid.

2) Using 5-bromo-1-(1-methylethyl)-2(1H)-pyrimidone obtained in the above reaction and the intermediate obtained in Example 4-1), the entitled compound was obtained in the same manner as in Example 4-2), 4-3) and 44).

$^1$HNMR (300 MHz, CDCl$_3$, δ ppm): 1.38-1.72 (12H, m), 1.81-1.90 (4H, m), 2.00-2.07 (2H, m), 2.31-2.37 (2H, m), 2.49-2.55 (1H, m), 2.78-2.81 (2H, m), 4.33-4.38 (1H, m), 5.08-5.15 (1H, m), 6.98 (2H, d, J=8.6 Hz), 7.30 (2H, d, J=8.6 Hz), 7.75 (1H, d, J=3.3 Hz), 8.78 (1H, d, J=3.3 Hz);

Mass Spectrum (ESI): 382(M+H).

Example 29

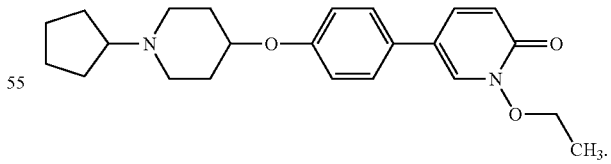

5-[4-(1-Cyclopentylpiperidin-4-yloxy)phenyl]-1-ethoxy-2(1H)-pyridone

Using the intermediate obtained in Example 4-1) and 5-bromo-1-ethoxy-2(1H)-pyridone, the entitled compound was obtained in the same manner as in Example 4-2), 4-3) and 4-4).

¹HNMR (300 MHz, CDCl₃, δ ppm): 1.39-1.73 (9H, m), 1.82-1.91 (4H, m), 2.00-2.06 (2H, m), 2.31-2.37 (2H, m), 2.50-2.55 (1H, m), 2.78-2.82 (2H, m), 4.33-4.43 (3H, m), 6.74 (1H, d, J=9.7 Hz), 6.95 (2H, d, J=8.8 Hz), 7.31 (2H, d, J=8.8 Hz), 7.56 (1H, dd, J=2.6, 9.5 Hz), 7.65 (1H, d, J=2.1 Hz); Mass Spectrum (ESI): 383 (M+H)

Example 30

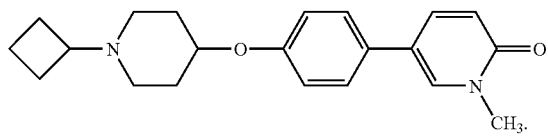

5-[4-(1-Cyclobutylpiperidin-4-yloxy)phenyl]-1-methyl-2(1H)-pyridone

Using the intermediate obtained in Example 4-1) and 5-bromo-1-methyl-2(1H)-pyridone, the entitled compound was obtained in the same manner as in Example 4-2), 4-3) and 44).

¹HNMR (300 MHz, CDCl₃, δ ppm): 1.65-1.93 (6H, m), 1.96-2.08 (4H, m), 2.13-2.17 (2H, m), 2.60-2.65 (2H, m), 2.72-2.77 (1H, m), 3.61 (3H, s), 4.33-4.36 (1H, m), 6.65 (1H, d, J=9.3 Hz), 6.95 (2H, d, J=8.8 Hz), 7.30 (2H, d, J=8.8 Hz), 7.42 (1H, d, J=2.6 Hz), 7.58 (1H, dd, J=2.6, 9.4 Hz);

Mass Spectrum (ESI): 339 (M+H).

Example 31

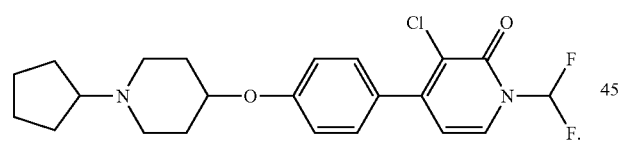

3-Chloro-4-[4-(1-cyclopentylpiperidin-4-yloxy)phenyl]-1-difluoromethyl-2(1H)-pyridone Using the intermediate obtained in Example 4-1) and 3-chloro-4-iodo-1-difluoromethyl-2(1H)-pyridone, the entitled compound was obtained in the same manner as in Example 4-2), 4-3) and 4-4).

¹HNMR (300 MHz, CDCl₃, δ ppm): 1.38-1.73 (6H, m), 1.83-1.93 (4H, m), 2.01-2.08 (2H, m), 2.32-2.38 (2H, m), 2.50-2.56 (1H, m), 2.79-2.84 (2H, m), 4.38-4.42 (1H, m), 6.37 (1H, d, J=7.4 Hz), 6.99 (2H, d, J=8.9 Hz), 7.41-7.47 (3H, m), 7.74 (1H, t, J=60.3 Hz);

Mass Spectrum (ESI): 423 (M+H).

Example 32

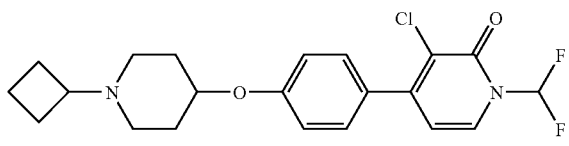

3-Chloro-4-[4-(1-cyclobutylpiperidin-4-yloxy)phenyl]-1-difluoromethyl-2(1H)-pyridone The entitled compound was obtained in the same manner as in Example 31, for which, however, cyclobutanone was used in place of cyclopentanone.

¹HNMR (300 MHz, CDCl₃, δ ppm): 1.61-1.93 (6H, m), 1.99-2.09 (4H, m), 2.14-2.21 (2H, m), 2.61-2.64 (2H, m), 2.72-2.78 (1H, m), 4.39-4.41 (1H, m), 6.37 (1H, d, J=7.4 Hz), 6.99 (2H, d, J=8.9 Hz), 7.41-7.48 (3H, m), 7.75 (1H, t, J=60.1 Hz);

Mass Spectrum (ESI): 409 (M+H).

Example 33

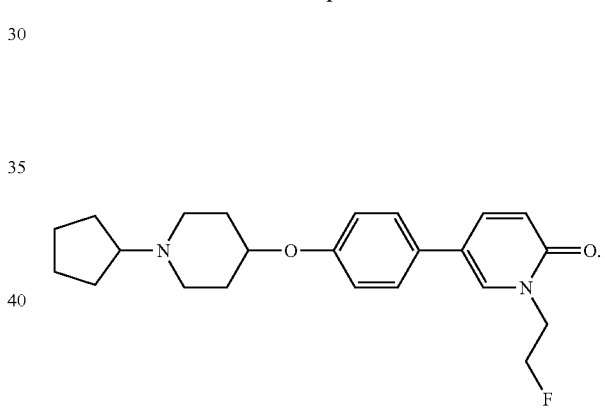

5-[4-(1-Cyclopentylpiperidin-4-yloxy)phenyl]-1-(2-fluoroethyl)-2(1H)-pyridone

Using the intermediate obtained in Example 4-1) and 5-bromo-1-(2-fluoroethyl)-2(1H)-pyridone, the entitled compound was obtained in the same manner as in Example 4-2), 4-3) and 4-4).

¹HNMR (300 MHz, CDCl₃, δ ppm): 1.39-1.73 (6H, m), 1.83-1.91 (4H, m), 2.00-2.06 (2H, m), 2.31-2.38 (2H, m), 2.50-2.53 (1H, m), 2.78-2.84 (2H, m), 4.25-4.37 (3H, m), 4.71 (2H, dt, J=4.6, 47.4 Hz), 6.67 (1H, d, J=9.5 Hz), 6.95 (2H, d, J=8.7 Hz), 7.31 (2H, d, J=8.7 Hz), 7.46 (1H, d, J=2.6 Hz), 7.62 (1H, dd, J=2.6, 9.5 Hz);

Mass Spectrum (ESI): 385 (M+H).

Example 34

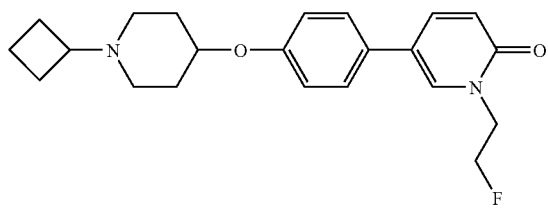

5-[4-(1-Cyclobutylpiperidin-4-yloxy)phenyl]-1-(2-fluoroethyl)-2(1H)-pyridone

The entitled compound was obtained in the same manner as in Example 33, for which, however, cyclobutanone was used in place of cyclopentanone.

$^1$HNMR (300 MHz, CDCl$_3$, δ ppm): 1.65-1.92 (6H, m), 1.96-2.07 (4H, m), 2.13-2.19 (2H, m), 2.60-2.63 (2H, m), 2.71-2.77 (1H, m), 4.24-4.36 (3H, m), 4.77 (2H, dt, J=4.6, 47.4 Hz), 6.66 (1H, d, J=9.5 Hz), 6.95 (2H, d, J=8.8 Hz), 7.31 (2H, d, J=8.8 Hz), 7.45 (1H, d, J=2.6 Hz), 7.62 (1H, dd, J=2.6, 9.4 Hz);

Mass Spectrum (ESI): 371 (M+H).

Example 35

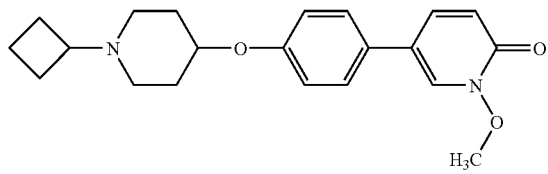

5-[4-(1-Cyclobutylpiperidin-4-yloxy)phenyl]-1-methoxy-2(1H)-pyridone

The entitled compound was obtained in the same manner as in Example 11, for which, however, cyclobutanone was used in place of cyclopentanone.

$^1$HNMR (300 MHz, CDCl$_3$, δ ppm): 1.66-1.92 (6H, m), 1.96-2.07 (4H, m), 2.14-2.19 (2H, m), 2.60-2.66 (2H, m), 2.71-2.77 (1H, m), 4.13 (3H, s), 4.34-4.36 (1H, m), 6.76 (1H, d, J=9.6 Hz), 6.95 (2H, d, J=8.8 Hz), 7.31 (2H, d, J=8.8 Hz), 7.57 (1H, dd, J=2.6, 9.5 Hz), 7.67 (1H, d, J=2.6 Hz);

Mass Spectrum (ESI): 355 (M+H).

Example 36

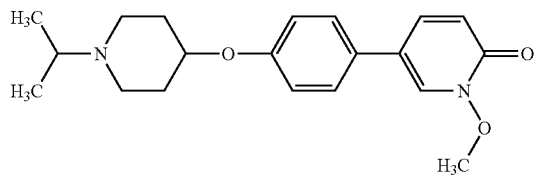

5-[4-(1-(1-Methylethyl)piperidin-4-yloxy)phenyl]-1-methoxy-2(1H)-pyridone

The entitled compound was obtained in the same manner as in Example 11, for which, however, acetone was used in place of cyclopentanone.

$^1$HNMR (300 MHz, CDCl$_3$, δ ppm): 1.09 (6H, d, J=6.6 Hz), 1.83-1.91 (2H, m), 2.06-2.11 (2H, m), 2.44-2.50 (2H, m), 2.79-2.85 (3H, m), 4.12 (3H, s), 4.34-4.37 (1H, m), 6.74 (1H, d, J=9.3 Hz), 6.95 (2H, d, J=8.7 Hz), 7.30 (2H, d, J=8.7 Hz), 7.56 (1H, dd, J=2.6, 9.5 Hz), 7.67 (1H, d, J=2.6 Hz);

Mass Spectrum (ESI): 343 (M+H).

Example 37

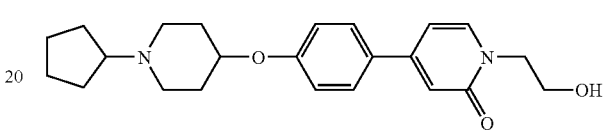

4-[4-(1-Cyclopentylpiperidin-4-yloxy)phenyl]-1-(2-hydroxyethyl)-2(1H)-pyridone

Using the intermediate obtained in Example 4-1) and 5-bromo-1-(2-hydroxyethyl)-2(1H)-pyridone, the entitled compound was obtained in the same manner as in Example 4-2), 4-3) and 4-4).

$^1$HNMR (300 MHz, CDCl$_3$, δ ppm): 1.39-1.73 (6H, m), 1.79-1.91 (4H, m), 1.97-2.06 (2H, m), 2.32-2.39 (2H, m), 2.50-2.56 (1H, m), 2.78-2.81 (2H, m), 3.73 (1H, brs), 3.97-4.00 (2H, m), 4.15-4.18 (2H, m), 4.35-4.40 (1H, m), 6.47 (1H, dd, J=2.0, 7.1 Hz), 6.78 (1H, d, J=1.8 Hz), 6.96 (2H, d, J=8.9 Hz), 7.36 (1H, d, J=7.1 Hz), 7.51 (2H, d, J=8.9 Hz);

Mass Spectrum (ESI): 383 (M+H).

Example 38

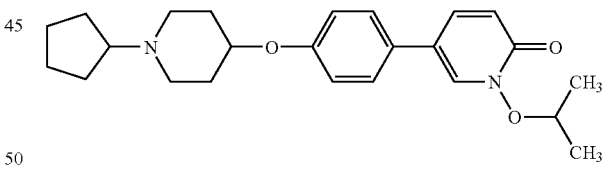

5-[4-(1-Cyclopentylpiperidin-4-yloxy)phenyl]-1-(1-methylethoxy)-2(1H)-pyridone

Using the intermediate obtained in Example 4-1) and 5-bromo-1-(1-methylethoxy)-2(1H)-pyridone, the entitled compound was obtained in the same manner as in Example 4-2), 4-3) and 4-4).

$^1$HNMR (300 MHz, CDCl$_3$, δ ppm): 1.25-1.59 (10H, m), 1.69-1.72 (2H, m), 1.83-1.91 (4H, m), 2.05-2.12 (2H, m), 2.41-2.43 (2H, m), 2.56-2.62 (1H, m), 2.82-2.84 (2H, m), 4.35-4.40 (1H, m), 4.84-4.92 (1H, m), 6.73 (1H, d, J=10.0 Hz), 6.95 (2H, d, J=8.8 Hz), 7.31 (2H, d, J=8.8 Hz), 7.54-7.57 (2H, m);

Mass Spectrum (ESI): 397 (M+H).

Example 39

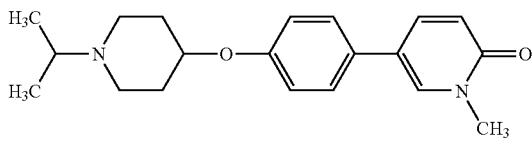

5-[4-(1-(1-Methylethyl)piperidin-4-yloxy)phenyl]-1-methyl-2(1H)-pyridone

Isopropyl iodide (0.125 mL, 1.25 mmol) was added to a dimethylformamide (5 mL) solution of the compound (250 mg, 0.83 mmol) obtained in Example 4-4) and potassium carbonate (288 mg, 2.08 mmol), and stirred at 90° C. for 10 hours. Water was added to the reaction mixture, and extracted twice with ethyl acetate. The organic layer was washed with saturated brine, dried with anhydrous magnesium sulfate and concentrated under reduced pressure. The residue was purified through amine-type silica gel chromatography (Biotage NH, ethyl acetate/hexane=1/1) to obtain the entitled compound (62 mg, 46%) as a pale yellow solid.

$^1$HNMR (300 MHz, CDCl$_3$, δ ppm): 1.11 (6H, d, J=6.5 Hz), 1.94-1.92 (2H, m), 2.06-2.13 (2H, m), 2.44-2.51 (2H, m), 2.79-2.88 (3H, m), 3.63 (3H, s), 4.35-4.39 (1H, m), 6.66 (1H, d, J=9.5 Hz), 6.96 (2H, d, J=8.8 Hz), 7.32 (2H, d, J=8.8 Hz), 7.44 (1H, d, J=2.6 Hz), 7.59 (1H, dd, J=2.6, 9.4 Hz);

Mass Spectrum (ESI): 327 (M+H).

Example 40

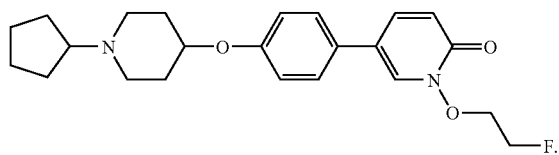

5-[4-(1-Cyclopentylpiperidin-4-yloxy)phenyl]-1-(2-fluoroethoxy)-2(1H)-pyridone

Using the intermediate obtained in Example 4-1) and 5-bromo-1-(2-fluoroethoxy)-2(1H)-pyridone, the entitled compound was obtained in the same manner as in Example 4-2), 4-3) and 4-4).

$^1$HNMR (300 MHz, CDCl$_3$, δ ppm): 1.46-1.77 (6H, m), 1.83-1.91 (4H, m), 2.06-2.12 (2H, m), 2.45-2.62 (3H, m), 2.81-2.85 (2H, m), 4.37-4.40 (1H, m), 4.56-4.82 (4H, m), 6.75 (1H, d, J=9.5 Hz), 6.96 (2H, d, J=8.8 Hz), 7.32 (2H, d, J=8.8 Hz), 7.59 (1H, dd, J=2.6, 9.5 Hz), 7.73 (1H, d, J=2.6 Hz);

Mass Spectrum (ESI): 401 (M+H).

Example 41

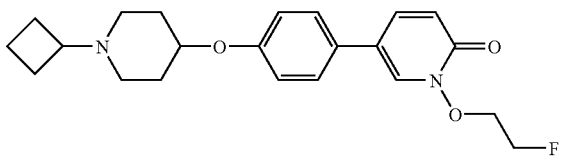

5-[4-(1-Cyclobutylpiperidin-4-yloxy)phenyl]-1-(2-fluoroethoxy)-2(1H)-pyridone

The entitled compound was obtained in the same manner as in Example 40, for which, however, cyclobutanone was used in place of cyclopentanone.

$^1$HNMR (300 MHz, CDCl$_3$, δ ppm): 1.64-1.92 (6H, m), 1.96-2.08 (4H, m), 2.13-2.20 (2H, m), 2.60-2.65 (2H, m), 2.71-2.74 (1H, m), 4.33-4.36 (1H, m), 4.56-4.81 (4H, m), 6.74 (1H, d, J=9.6 Hz), 6.95 (2H, d, J=8.8 Hz), 7.31 (2H, d, J=8.8 Hz), 7.58 (1H, dd, J=2.7, 9.5 Hz), 7.72 (1H, d, J=2.7 Hz);

Mass Spectrum (ESI): 387 (M+H).

Example 42

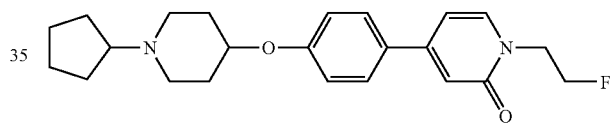

4-[4-(1-Cyclopentylpiperidin-4-yloxy)phenyl]-1-(2-fluoroethyl)-2(1H)-pyridone

Using the intermediate obtained in Example 4-1) and 4-iodo-1-(2-fluoroethyl)-2(1H)-pyridone, the entitled compound was obtained in the same manner as in Example 4-2), 4-3) and 4-4).

$^1$HNMR (300 MHz, CDCl$_3$, δ ppm): 1.39-1.73 (6H, m), 1.84-1.91 (4H, m), 2.01-2.07 (2H, m), 2.32-2.39 (2H, m), 2.50-2.56 (1H, m), 2.79-2.82 (2H, m), 4.26 (2H, dt, J=4.6, 27.8 Hz), 4.37-4.39 (1H, m), 4.76 (2H, dt, J=4.6, 42.3 Hz), 6.44 (1H, dd, J=2.0, 7.1 Hz), 6.76 (1H, d, J=1.8 Hz), 6.97 (2H, d, J=8.9 Hz), 7.34 (1H, d, J=7.0 Hz), 7.52 (2H, d, J=8.9 Hz);

Mass Spectrum (ESI): 385 (M+H).

Example 43

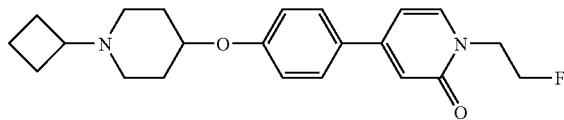

4-[4-(1-Cyclobutylpiperidin-4-yloxy)phenyl]-1-(2-fluoroethyl)-2(1H)-pyridone

The entitled compound was obtained in the same manner as in Example 42, for which, however, cyclobutanone was used in place of cyclopentanone.

$^1$HNMR (300 MHz, CDCl$_3$, δ ppm): 1.66-1.93 (6H, m), 1.98-2.07 (4H, m), 2.14-2.21 (2H, m), 2.62-2.63 (2H, m), 2.72-2.78 (1H, m), 4.27 (2H, dt, J=4.5, 27.8 Hz), 4.37-4.40 (1H, m), 4.76 (2H, dt, J=4.5, 47.5 Hz), 6.44 (1H, dd, J=2.0, 7.0 Hz), 6.76 (1H, d, J=2.0 Hz), 6.97 (2H, d, J=8.8 Hz), 7.35 (1H, d, J=7.0 Hz), 7.52 (2H, d, J=8.8 Hz);

Mass Spectrum (ESI): 371 (M+H).

Example 44

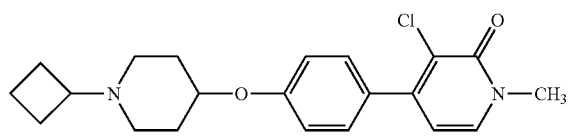

3-Chloro-4-[4-(1-cyclobutylpiperidin-4-yloxy)phenyl]-1-methyl-2(1H)-pyridone

Using the intermediate obtained in Example 4-1) and 3-chloro-4-iodo-1-methyl-2(1H)-pyridone, the entitled compound was obtained in the same manner as in Example 4-2), 4-3) and 44).

$^1$HNMR (300 MHz, CDCl$_3$, δ ppm): 1.65-1.74 (2H, m), 1.82-1.93 (4H, m), 1.98-2.08 (4H, m), 2.13-2.20 (2H, m), 2.61-2.77 (3H, m), 3.63 (3H, s), 4.37-4.39 (1H, m), 6.20 (1H, d, J=7.0 Hz), 6.96 (2H, d, J=8.8 Hz), 7.23 (1H, d, J=7.0 Hz), 7.42 (2H, d, J=8.8 Hz);

Mass Spectrum (ESI): 373 (M+H).

Example 45

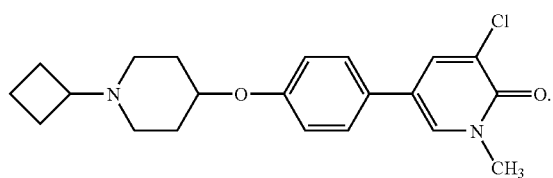

3-Chloro-5-[4-(1-cyclobutylpiperidin-4-yloxy)phenyl]-1-methyl-2(1H)-pyridone

Using the intermediate obtained in Example 4-1) and 3-chloro-5-iodo-1-methyl-2(1H)-pyridone, the entitled compound was obtained in the same manner as in Example 4-2), 4-3) and 4-4).

$^1$HNMR (300 MHz, CDCl$_3$, 5 ppm): 1.66-1.94 (6H, m), 1.98-2.10 (4H, m), 2.15-2.19 (2H, m), 2.62-2.78 (3H, m), 3.68 (3H, s), 4.34-4.37 (1H, m), 6.95 (2H, d, J=8.8 Hz), 7.29 (2H, d, J=8.8 Hz), 7.38 (1H, d, J=2.5 Hz), 7.79 (1H, d, J=2.5 Hz);

Mass Spectrum (ESI): 373 (M+H).

Example 46

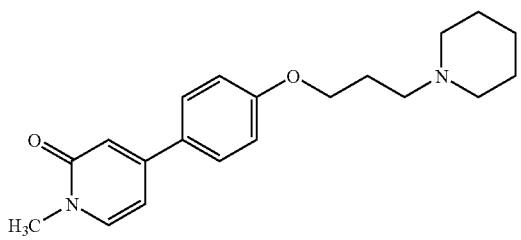

1-Methyl-4-{4-[3-(1-piperidinyl)propoxy]phenyl}-2(1H)-pyridone

1) Production of 4-(4,4,5,5-tetramethyl-1,3,2-dioxoborolan-2-yl)-1-(2-tetrahydropyranyloxy)benzene Potassium acetate (5.8 g, 59.2 mmol) and bis(diphenylphosphino)ferrocene palladium(II) dichloride-dichloromethane (806 mg, 0.99 mmol) were added to a dimethyl sulfoxide (70 mL) solution of 4-iodophenol tetrahydropyranyl ether (6.0 g, 19.7 mmol) readily preparable from 4-iodophenol and dihydropyran, and bis(pinacolato)diboron (6.01 g, 23.7 mmol), and stirred in a nitrogen atmosphere at 75° C. for 1 hour. The reaction mixture was cooled to room temperature, water was added to it, and extracted with ethyl acetate. The organic layer was washed with water and saturated brine, dried with anhydrous magnesium sulfate, and concentrated under reduced pressure. The residue was purified through silica gel column chromatography (C-300, hexane/ethyl acetate=8/1) to obtain the entitled compound (4.54 g, 76%).

2) Production of 4-{4-(2-tetrahydropyranyloxy)phenyl}-1-methyl-2(1H)-pyridone 2N sodium carbonate (4.0 mL) and tetrakis(triphenylphosphine)palladium(0) (246 mg, 0.21 mmol) were added to a dimethoxyethane (30 mL) solution of the compound (1.42 g, 4.68 mmol) obtained in the above reaction and 1-methyl-4-iodo-2(1H)-pyridone (1.0 g, 4.25 mmol), and stirred in a nitrogen atmosphere at 90° C. for 17 hours. The reaction mixture was cooled to room temperature, and extracted with ethyl acetate. The organic layer was washed with water, saturated sodium bicarbonate water and saturated brine in that order, then dried with anhydrous magnesium sulfate and concentrated under reduced pressure. The residue was purified through silica gel column chromatography (C-300, ethyl acetate/hexane=3/1) to obtain the entitled compound (1.01 g, 83%).

3) Production of 4-{(4-hydroxy)phenyl}-1-methyl-2(1H)-pyridone

Pyridinium p-toluenesulfonate (2.67 g, 10.6 mmol) was added to an ethanol (15 mL) solution of the compound (1.01 g, 3.54 mmol) obtained in the above reaction, and stirred at room temperature for 19 hours. Water was added to the reaction mixture, the precipitated substance was taken out through filtration, washed with diethyl ether, and dried to obtain the entitled compound (500 mg, 70%) as a colorless solid. Further, the filtrate was extracted with ethyl acetate, the organic layer was washed with saturated brine, dried with anhydrous magnesium sulfate and concentrated under reduced pressure to obtain the entitled compound (195 mg, 27%).

4) Production of 4-{4-(3-chloropropoxy)phenyl}-1-methyl-2(1H)-pyridone

1-Bromo-3-chloropropane (0.48 mL, 4.84 mmol) and potassium carbonate (1.19 g, 8.63 mmol) were added to an acetone (15 mL)/tetrahydrofuran (5 mL) solution of the compound (695 mg, 3.45 mmol) obtained in the above reaction, and stirred under reflux for 4 hours. The reaction mixture was cooled to room temperature, water was added to it, and extracted with ethyl acetate. The organic layer was washed with saturated brine, dried with anhydrous magnesium sulfate and concentrated under reduced pressure. The residue was purified through silica gel column chromatography (C-300, ethyl acetate/hexane=3/1) to obtain the entitled compound (720 mg, 75%).

5) Using the compound (695 mg, 3.45 mmol) obtained in the above reaction and piperidine (0.12 mL), the entitled compound (169 mg, 50%) was obtained as a colorless solid in the same manner as in Example 1-5).

$^1$HNMR (300 MHz, CDCl$_3$, δ ppm): 1.45-1.47 (2H, m), 1.57-1.64 (4H, m), 1.80 (1H, brs), 1.98-2.03 (2H, m), 2.41-2.51 (5H, m), 3.58 (3H, s), 4.06 (2H, t, J=6.4 Hz), 6.42 (1H, dd, J=2.0, 7.0 Hz), 6.77 (1H, d, J=2.0 Hz), 6.97 (2H, d, J=8.8 Hz), 7.31 (1H, d, J=7.0 Hz), 7.53 (2H, d, J=8.8 Hz);

Mass Spectrum (ESI): 327 (M+H).

Example 47

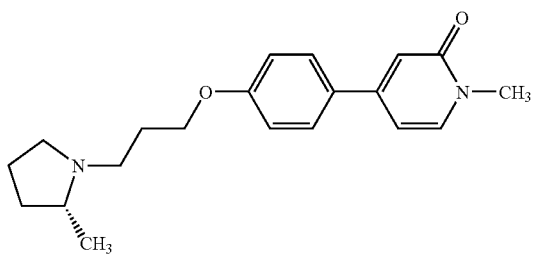

1-Methyl-4-{4-[3-((2S)-2-methyl-1-pyrrolidinyl)propoxy]phenyl}-2(1H)-pyridone

Using the intermediate obtained in Example 46-4) and (2S)-2-methylpyrrolidine, the entitled compound was obtained in the same manner as in Example 46-5).

$^1$HNMR (400 MHz, CDCl$_3$, δ ppm): 1.10 (3H, d, J=6.1 Hz), 1.43 (1H, m), 1.70-2.33 (8H, m), 2.96-3.03 (1H, m), 3.17-3.22 (1H, m), 3.57 (3H, s), 4.06-4.09 (2H, m), 6.41-6.43 (1H, m), 6.76 (1H, d, J=2.0 Hz), 6.95-6.98 (2H, m), 7.30-7.31 (1H, m), 7.50-7.53 (2H, m);

Mass Spectrum (ESI): 327 (M+H).

Reference Example 1

5-Bromo-1-methyl-2(1H)-pyridone

With cooling with ice, potassium carbonate (5.96 g, 43.1 mmol) and methyl iodide (1.29 mL, 20.7 mmol) were added to a dimethylformamide (50 mL) solution of 5-bromo-2-hydroxypyridine (3.0 g, 7.24 mmol), and stirred at that temperature for 16 hours. Water was added to the reaction mixture, and extracted three times with ethyl acetate. The organic layer was washed with saturated brine, dried with anhydrous sodium sulfate and concentrated under reduced pressure. The residue was purified through silica gel column chromatography (C-300, ethyl acetate/hexane=1/1) to obtain the entitled compound (2.92 g, 90%) as a colorless oil.

Reference Example 2

5-Bromo-1-ethoxy-2(1H)-pyridone

1) Production of 5-bromo-2-chloropyridine-N-oxide

With cooling with ice, trifluoroacetic anhydride (11.9 mL, 84.2 mmol) was added to a chloroform (50 mL) solution of 5-bromo-2-chloropyridine (8.1 g, 42.1 mmol) and percarbamide (8.3 g, 88.4 mmol), and stirred at room temperature for 1 hour. Sodium thiosulfate water was added to the reaction mixture, then stirred at room temperature for 40 minutes, and extracted twice with chloroform. The organic layer was washed with saturated sodium bicarbonate water and saturated brine, dried with anhydrous sodium sulfate and concentrated under reduced pressure. Ethyl acetate was added to the residue, and the resulting solid was taken out through filtration, washed with diethyl ether and dried to obtain the entitled compound (6.85 g, 78%) as a yellow solid.

2) Production of 5-bromo-1-hydroxy-2(1H)-pyridone

Trifluoroacetic anhydride (16 mL) was added to a chloroform (8 mL) solution of the compound (2.0 g, 10.4 mmol) obtained in the above reaction, and stirred at 60° C. for 4 hours. The reaction mixture was cooled to room temperature, and concentrated under reduced pressure. Saturates sodium bicarbonate water and methanol were added to the residue, stirred at room temperature for 40 minutes, and the mixture was filtered through silica gel. The filtrate was concentrated, methanol and diethyl ether were added to the residue, and the suspension was filtered and dried to obtain the entitled compound (1.96 g, 99%) as a solid.

3) Ethyl iodide (0.25 mL, 31.6 mmol) was added to a dimethyl sulfoxide (4 mL) solution of the compound (400 mg, 2.10 mmol) obtained in the above reaction and potassium carbonate (5.96 g, 43.1 mmol), and stirred at room temperature for 6 hours. Water was added to the reaction mixture, and extracted twice with ethyl acetate. The organic layer was washed with saturated brine, dried with anhydrous sodium sulfate, and concentrated under reduced pressure. The residue was purified through silica gel column chromatography (C-300, ethyl acetate/hexane=3/2) to obtain the entitled compound (295 mg, 64%) as a pale yellow oil.

Reference Example 3

1-Difluoromethyl-3-chloro-4-iodo-2(1H)-pyridone

1) Production of 2,3-dichloro-4-iodopyridine

With cooling with ice, 2.66 M n-butyllithium (100 mL, 0.266 mmol) was added to a tetrahydrofuran (400 mL) solution of diisopropylamine (11.9 mL, 84.2 mmol), cooled to −70° C., and stirred for 0.5 hours. A tetrahydrofuran (170 mL) solution of 2,3-dichloropyridine (35 g, 0.24 mmol) was dropwise added to the solution, over 25 minutes, and then stirred at −70° C. for 1 hour. A tetrahydrofuran (170 mL) solution of iodine (75 g, 0.30 mmol) was added to the reaction mixture, and warmed up to room temperature with stirring. Water was added to the reaction mixture, and extracted twice with ethyl acetate. The organic layer was washed with saturated brine, dried with anhydrous sodium sulfate, and concentrated under reduced pressure. Ethyl acetate and hexane were added to the residue, the precipitated matter was taken out through filtration and dried to obtain the entitled compound (46.4 g, 72%) as a pale yellow solid.

2) At 40° C., an acetonitrile (5 mL) solution of 2,2-difluoro-2-(fluorosulfonyl)acetic acid was dropwise added to an acetonitrile (22 mL) suspension of the compound (3.0 g, 10.9 mmol) obtained in the above reaction and sodium hydrogencarbonate (1.84 g, 21.9 mmol), over 3 hours. Aqueous sodium bicarbonate was added to the reaction mixture, and extracted twice with ethyl acetate. The organic layer was washed with saturated brine, dried with anhydrous sodium sulfate, and concentrated under reduced pressure. The residue was purified through silica gel column chromatography (C-300, ethyl acetate) to obtain the entitled compound (1.14 g, 38%) as a pale yellow solid.

INDUSTRIAL APPLICABILITY

The compounds and pharmaceutically-acceptable salts thereof of the invention have a strong histamine-H3 receptor antagonistic activity or inverse-agonistic activity, and are useful for treatment and/or prevention of metabolic system diseases such as obesity, diabetes, hormone secretion disorder, hyperlipemia, gout, fatty liver; circulatory system diseases such as stenocardia, acute/congestive cardiac insufficiency, cardiac infarction, coronary arteriosclerosis, hypertension, nephropathy, sleep disorder, various diseases accompanied by sleep disorder, for example, idiopathic hypersomnia, repetitive hypersomnia, true hypersomnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, electrolyte abnormality; central or peripheral nervous system diseases such as bulimia, emotional disorder, depression, anxiety, epilepsy, delirium, dementia, schizophrenia, attention deficit/hyperactivity disorder, memory disorder, Alzheimer's disease, Parkinson's disease, sleep disorder, cognition disorder, motion disorder, paresthesia, dysosmia, epilepsy, morphine resistance, drug dependency, alcoholism; and tremor.

The invention claimed is:

1. A compound of the formula (I):

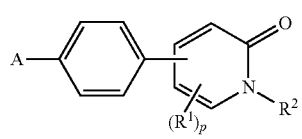

(I)

wherein:

A represents a group of the formula (III-1):

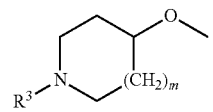

(III-1)

or the formula (III-2):

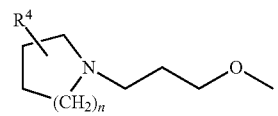

(III-2)

wherein $R^3$ represents a hydrogen atom, or a cycloalkyl group optionally substituted with a lower alkyl group, a halo-lower alkyl group, a cycloalkyl group, a halogen atom or a hydroxyl group;

$R^4$ represents a hydrogen atom, a hydroxyl group, a halogen atom, a lower alkyl group, a halo-lower alkyl group, a lower alkoxy group, a halo-lower alkoxy group, a lower alkoxy-lower alkyl group, or a halo-lower alkoxy-lower alkyl group;

m is 0 or 1;

n is 0, 1 or 2;

$R^1$ each independently represents a hydrogen atom, a hydroxyl group, a halogen atom, a lower alkyl group, a halo-lower alkyl group, a lower alkoxy group, a halo-lower alkoxy group, a lower alkoxy-lower alkyl group, or a halo-lower alkoxy-lower alkyl group;

$R^2$ represents a hydroxyl group, a halogen atom, a lower alkyl group, a halo-lower alkyl group, a lower alkoxy group, a halo-lower alkoxy group, a lower alkoxy-lower alkyl group, or a halo-lower alkoxy-lower alkyl group;

p is an integer from 0 to 4;

or a pharmaceutically acceptable salt thereof.

2. The compound of claim 1 of the formula (I-1):

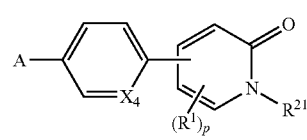

(I-1)

wherein:

$R^{21}$ represents a hydroxyl group, a halogen atom, a lower alkyl group, a halo-lower alkyl group, a lower alkoxy group, a halo-lower alkoxy group, a lower alkoxy-lower alkyl group, or a halo-lower alkoxy-lower alkyl group.

3. The compound of claim 1 wherein A is a group of the formula (III-1):

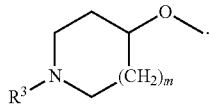
(III-1)

4. The compound of claim 1 wherein A is a group of the formula (III-2):

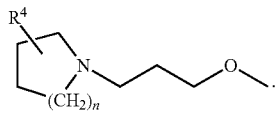
(III-2)

5. A compound which is selected from the group consisting of:
1-methyl-5-{4-[3-(1-piperidinyl)propoxy]phenyl}-2(1H)-pyridone,
1-difluoromethyl-5-{4-[3-(1-piperidinyl)propoxy]phenyl}-2(1H)-pyridone,
1-difluoromethyl-4-{4-[3-(1-piperidinyl)propoxy]phenyl}-2(1H)-pyridone,
5-[4-(1-cyclopentylpiperidin-4-yloxy)phenyl]-1-methyl-2(1H)-pyridone,
5-[4-(1-cyclopentylpiperidin-4-yloxy)phenyl]-1-difluoromethyl-2(1H)-pyridone,
4-[4-(1-cyclopentylpiperidin-4-yloxy)phenyl]-1-difluoromethyl-2(1H)-pyridone,
4-[4-(1-cyclopentylpiperidin-4-yloxy)phenyl]-1-methyl-2(1H)-pyridone,
4-[4-(1-cyclopentylpiperidin-4-yloxy)phenyl]-1-ethyl-2(1H)-pyridone,
4-[4-(1-cyclopentylpiperidin-4-yloxy)phenyl]-1-(1-methylethyl)-2(1H)-pyridone,
4-[4-(1-cyclobutylpiperidin-4-yloxy)phenyl]-1-difluoromethyl-2(1H)-pyridone,
5-[4-(1-cyclopentylpiperidin-4-yloxy)phenyl]-1-methoxy-2(1H)-pyridone,
5-[4-(1-cyclopentylpiperidin-4-yloxy)phenyl]-1,3-dimethyl-2(1H)-pyridone,
4-[4-(1-cyclopentylpiperidin-4-yloxy)phenyl]-1-(2,2-difluoroethyl)-2(1H)-pyridone,
4-[4-(1-cyclopropylpiperidin-4-yloxy)phenyl]-1-difluoromethyl-2(1H)-pyridone,
6-[4-(1-cyclopentylpiperidin-4-yloxy)phenyl]-1-methyl-2(1H)-pyridone,
3-[4-(1-cyclopentylpiperidin-4-yloxy)phenyl]-1-methyl-2(1H)-pyridone,
1-[4-(1-cyclopentylpiperidin-4-yloxy)phenyl]-2(1H)-pyridone,
5-bromo-3-[4-(1-cyclopentylpiperidin-4-yloxy)phenyl]-1-methyl-2(1H)-pyridone,
1-[4-(1-cyclopentylpiperidin-4-yloxy)phenyl]-4-methyl-2(1H)-pyridone,
3-[4-(1-cyclopentylpiperidin-4-yloxy)phenyl]-1,6-dimethyl-2(1H)-pyridone,
5-[4-(1-cyclopentylpiperidin-4-yloxy)phenyl]-1,6-dimethyl-2(1H)-pyridone,
5-[4-(1-cyclopentylpiperidin-4-yloxy)phenyl]-1,4-dimethyl-2(1H)-pyridone,
5-chloro-3-[4-(1-cyclopentylpiperidin-4-yloxy)phenyl]-1-methyl-2(1H)-pyridone,
5-[4-(1-cyclopentylpiperidin-4-yloxy)phenyl]-1-ethyl-2(1H)-pyridone,
5-[4-(1-cyclopentylpiperidin-4-yloxy)phenyl]-1-(1-methylethyl)-2(1H)-pyridone,
5-[4-(1-cyclopentylpiperidin-4-yloxy)phenyl]-1-ethoxy-2(1H)-pyridone,
5-[4-(1-cyclobutylpiperidin-4-yloxy)phenyl]-1-methyl-2(1H)-pyridone,
3-chloro-4-[4-(1-cyclopentylpiperidin-4-yloxy)phenyl]-1-difluoromethyl-2(1H)-pyridone,
3-chloro-4-[4-(1-cyclobutylpiperidin-4-yloxy)phenyl]-1-difluoromethyl-2(1H)-pyridone,
5-[4-(1-cyclopentylpiperidin-4-yloxy)phenyl]-1-(2-fluoroethyl)-2(1H)-pyridone,
5-[4-(1-cyclobutylpiperidin-4-yloxy)phenyl]-1-(2-fluoroethyl)-2(1H)-pyridone,
5-[4-(1-cyclobutylpiperidin-4-yloxy)phenyl]-1-methoxy-2(1H)-pyridone,
5-[4-(1-(1-methylethyl)piperidin-4-yloxy)phenyl]-1-methoxy-2(1H)-pyridone,
4-[4-(1-cyclopentylpiperidin-4-yloxy)phenyl]-1-(2-hydroxyethyl)-2(1H)-pyridone,
5-[4-(1-cyclopentylpiperidin-4-yloxy)phenyl]-1-(1-methylethoxy)-2(1H)-pyridone,
5-[4-(1-(1-methylethyl)piperidin-4-yloxy)phenyl]-1-methyl-2(1H)-pyridone,
5-[4-(1-cyclopentylpiperidin-4-yloxy)phenyl]-1-(2-fluoroethoxy)-2(1H)-pyridone,
5-[4-(1-cyclobutylpiperidin-4-yloxy)phenyl]-1-(2-fluoroethoxy)-2(1H)-pyridone,
4-[4-(1-cyclopentylpiperidin-4-yloxy)phenyl]-1-(2-fluoroethyl)-2(1H)-pyridone,
4-[4-(1-cyclobutylpiperidin-4-yloxy)phenyl]-1-(2-fluoroethyl)-2(1H)-pyridone,
3-chloro-4-[4-(1-cyclobutylpiperidin-4-yloxy)phenyl]-1-methyl-2(1H)-pyridone,
3-chloro-5-[4-(1-cyclobutylpiperidin-4-yloxy)phenyl]-1-methyl-2(1H)-pyridone,
1-methyl-4-{4-[3-(1-piperidinyl)propoxy]phenyl}-2(1H)-pyridone,
1-methyl-4-{4-[3-((2S)-2-methyl-1-pyrrolidinyl)propoxy]phenyl}-2(1H)-pyridone,
1-methyl-4-{4-[3-((2R)-2-methyl-1-pyrrolidinyl)propoxy]phenyl}-2(1H)-pyridone,
1-methyl-4-{4-[3-((3R)-3-methyl-1-piperidinyl)propoxy]phenyl}-2(1H)-pyridone,
1-ethyl-4-{4-[3-((3R)-3-methyl-1-piperidinyl)propoxy]phenyl}-2(1H)-pyridone,
1-methyl-5-{4-[3-((3R)-3-methyl-1-piperidinyl)propoxy]phenyl}-2(1H)-pyridone, and
1-ethyl-5-{4-[3-((3R)-3-methyl-1-piperidinyl)propoxy]phenyl}-2(1H)-pyridone,
or a pharmaceutically acceptable salt thereof.

6. A pharmaceutical composition which comprises an inert carrier and a compound of claim 1 or a pharmaceutically acceptable salt thereof.

7. A pharmaceutical composition which comprises an inert carrier and a compound of claim 5 or a pharmaceutically acceptable salt thereof.

* * * * *